US008435764B2

(12) United States Patent
Ding et al.

(10) Patent No.: US 8,435,764 B2
(45) Date of Patent: May 7, 2013

(54) MULTIPLEX DETECTION OF HEPATITIS VIRUS VARIATIONS

(75) Inventors: Chunming Ding, Singapore (SG); Ju Luan, Hong Kong (CN); Boping Zhou, Guangdong (CN); Jing Yuan, Guangdong (CN); Xinchun Chen, Guangdong (CN); Hongmei Zhang, Guangdong (CN)

(73) Assignees: The Chinese University of HongKong, HongKong (CN); The Third People's Hospital of Shenzhen, Guangdong (CN)

( * ) Notice: Subject to any disclaimer, the term of this patent is extended or adjusted under 35 U.S.C. 154(b) by 220 days.

(21) Appl. No.: 12/773,095

(22) Filed: May 4, 2010

(65) Prior Publication Data

US 2010/0286291 A1 Nov. 11, 2010

Related U.S. Application Data

(60) Provisional application No. 61/175,827, filed on May 6, 2009.

(51) Int. Cl.
*C12P 19/34* (2006.01)
*C12Q 1/68* (2006.01)
*C07H 21/04* (2006.01)

(52) U.S. Cl.
USPC ...... 435/91.2; 435/6.12; 435/91.33; 536/24.3

(58) Field of Classification Search .................. None
See application file for complete search history.

(56) References Cited

PUBLICATIONS

Luan et al. (Jun. 18, 2009) Multiplex Detection of 60 Hepatitis B Virus Variants by MALDI-TOF Mass spectrometry Clinical Chemistry vol. 55 issue 8 pp. 1503-1509.*
Seigneres, B. et al., Evolution of hepatitis B virus polymerase gene sequence during famciclovir therapy for chronic hepatitis B. The Journal of Infectious Diseases 2000;181: 1221-33,.
Stuyver, LJ, et al., Nomenclature for antiviral-resistant human hepatitis B virus mutations in the polymerase region. Hepatology, 2001;33;751-7.
Warner, N, et al., The L80I substitution in the reverse transcriptase domain of the hepatitis B virus polymerase is associated with lamivudine resistance and enhanced viral replication in vitro. Antimicrobial Agents and Chemotherapy 2007;51:2285-92.
Allen, MI, et al., Identification and characterization of mutations in hepatitis B virus resistant to lamivudine. Lamivudine Clinical Investigation Group. Hepatology,1998;27:1670-7.
Bartholomeusz, A, et al., Hepatitis B virus mutations associated with antiviral therapy. Journal of Medical Virology 2006;78 Suppl 552-555.
Locarnini, S. Hepatitis B viral resistance: mechanisms and diagnosis. J . of Hepatology vol. 39 supplement 1 pp. 124-132 (2003).

(Continued)

*Primary Examiner* — Samuel Woolwine
*Assistant Examiner* — Suchira Pande
(74) *Attorney, Agent, or Firm* — Ping Wang; Andrews Kurth, LLP

(57) ABSTRACT

Disclosed is a method for the detection of virus variations. Disclosed also is a method for the treatment of virus infection in a subject based on the detection of virus variations. Additionally, a kit is provided for the detection of virus variations.

11 Claims, 12 Drawing Sheets

Examples of a) MS detected both wild type and mutant sequences while sequencing only detected one sequence; b) sequencing detected both wild type and mutant sequences while MS only detected one sequence.

PUBLICATIONS

Westland, CE, et al., Week 48 resistance surveillance in two phase 3 clinical studies of adefovir dipivoxil for chronic hepatitis B. Hepatology, 2003;38:96-103.

Melegari, M, et al., Hepatitis B virus mutants associated with 3TC and famciclovir administration are replication defective. Hepatology, 1998;27:628-33.

Tenney, DJ, et al., Clinical emergence of entecavir-resistant hepatitis B virus requires additional substitutions in virus already resistant to Lamivudine. Antimicrobial Agents and Chemotherapy 2004;48:3498-507.

Delaney, W.E, et al., The hepatitis B virus polymerase mutation rtV173L is selected during lamivudine therapy and enhances viral replication in vitro. Journal of Virology 2003;77:11833-41.

Cane, P A, et al., Analysis of hepatitis B virus quasispecies changes during emergence and reversion of lamivudine resistance in liver transplantation (Abstract). Antiviral Therapy 1999;4:7-14.

Ono, S K, et al., The polymerase L528M mutation cooperates with nucleotide binding-site mutations, increasing hepatitis B virus replication and drug resistance. The Journal of Clinical Investigation 2001;107:449-55.

Yatsuji, H, et al., Emergence of a novel lamivudine-resistant hepatitis B virus variant with a substitution outside the YMDD motif. Antimicrobial Agents and Chemotherapy 2006;50:3867-74.

Sheldon, J,, et al., Selection of hepatitis B virus polymerase mutations in HIV-coinfected patients treated with tenofovir. Antiviral Therapy 2005;10:727-34,.

Bozdayi, A M, et al YSDD: a novel mutation in HBV DNA polymerase confers clinical resistance to lamivudine. Journal of Viral Hepatitis 2003;10:256-65.

Zollner, B, et al., Prevalence, incidence, and clinical relevance of the reverse transcriptase V207I mutation outside the YMDD motif of the hepatitis B virus polymerase during lamivudine therapy, Journal of Clinical Microbiology 2005;43:2503-5.

Pallier, C, et al., Dynamics of hepatitis B virus resistance to lamivudine. Journal of Virology 2006;80:643-53.

Bartholomeusz, A, et al., Antiviral drug resistance: clinical consequences and molecular aspects. Seminars in Liver Disease 2006;26: 162-70.

Pollicino, T, et al., Variability of the HBV pol gene reverse-transcriptase domain in viral isolates from untreated and lamivudine-resistant chronic hepatitis B patients [Abstract]. Digestive and Liver Disease 2007;39(3): A7.

Ahn, S H, et al. Evolution of viral quasispecies in the polymerase gene of hepatitis B virus during antiviral treatment: from naive to viral breakthrough [Abstract]. Hepatology 2007; 46(81): 642A-643A.

Tan, J, et al., Tenofovir monotherapy is effective in hepatitis B patients with antiviral treatment failure to adefovir in the absence of adefovir-resistant mutations. Journal of Hepatology 2008;48:391-8.

Yang, H, et al. Resistance surveillance in chronic hepatitis B patients treated with adefovir dipivoxil for up to 60 weeks. Hepatology 2002;36:464-73.

Liu, C.J, et al., Hepatitis B virus variants in patients receiving lamivudine treatment with breakthrough hepatitis evaluated by serial viral loads and full-length viral sequences. Hepatology 2001;34:583-9.

Schildgen, O, et al. Variant of hepatitis B virus with primary resistance to adefovir. The New England Journal of Medicine 2006;354:1807-12.

Angus, P, et al. Resistance to adefovir dipivoxil therapy associated with the selection of a novel mutation in the HBV polymerase. Gastroenterology 2003;125:292-7.

Chen, Rym, et al., Effect of the G1896A precore mutation on drug sensitivity and replication yield of lamivudine-resistant HBV in vitro. Hepatology 2003;37:27-35.

Tacke, F, et al., Basal core promoter and precore mutations in the hepatitis B virus genome enhance replication efficacy of Lamivudine-resistant mutants. Journal of Virology 2004;78:8524-35.

Chen, C.J, et al., Risk of hepatocelinlar carcinoma across a biological gradient of serum hepatitis B virus DNA level. Jama 2006;295:65-73.

Iloeje, UH, et al., Predicting cirrhosis risk based on the level of circulating hepatitis B viral load. Gastroenterology 2006;130:678-86.

Chen, G, et al., Past HBV viral load as predictor of mortality and morbidity ffrom HCC and chronic liver disease in a prospective study. Am J Gastroenterol 2006;101: 1797-803.

Chan, HL-Y, et al. High viral load and hepatitis B virus subgenotype Ce are associated with increased risk of hepatocellular carcinoma. J Clin Oncol 2008;26: 177-82.

Lok, ASF, et al. Long-term safety of lamivudine treatment in patients with chronic hepatitis B. Gastroenterology 2003;125:1714-22.

\* cited by examiner

Extension reaction thermal profile

94°C for 30 seconds

94°C for 5 seconds

52°C for 5 seconds  
80°C for 5 seconds  } 5 cycles } 40 cycles

72°C for 3 minutes

4°C forever

LIST OF SEQUENCES IDS OF HBV FULL LENGTH GENOME ENTRIES IN GENBANK.

| Genotype | A | B | C | D | E | F |
|---|---|---|---|---|---|---|
| | AB116087 | AF282918 | AB113878 | AB090269 | AB116654 | AB036911 |
| | AB116078 | AY217365 | AB026814 | AB109476 | AB205189 | AB036920 |
| | AB116080 | AF282917 | AB113876 | AB222713 | AB219534 | |
| | | AY217356 | AB033557 | DQ315778 | | |
| | | AB115551 | AB112471 | | | |
| | | AY217359 | DQ089765 | | | |
| | | AY217363 | AY217376 | | | |
| | | DQ448619 | DQ089757 | | | |
| | | AB033554 | DQ089761 | | | |
| | | AY217369 | | | | |

FIG. 4E

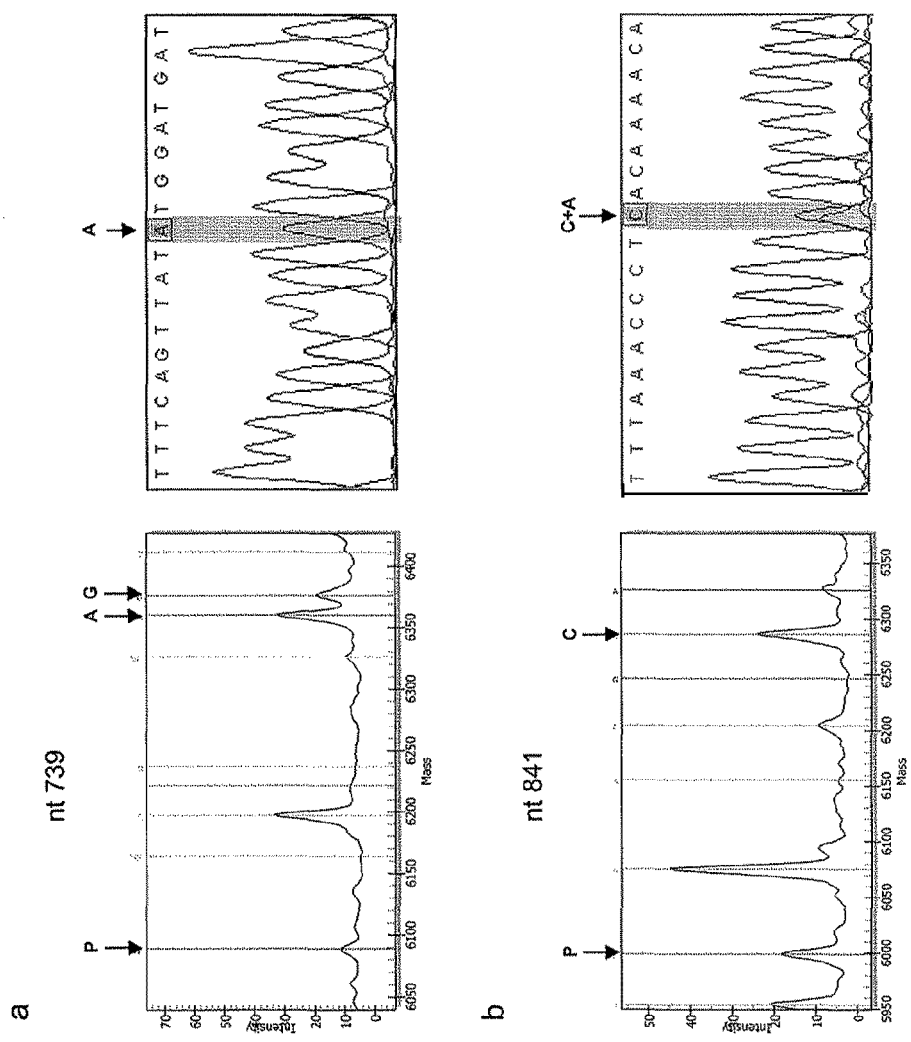
Figure 5 Examples of a) MS detected both wild type and mutant sequences while sequencing only detected one sequence; b) sequencing detected both wild type and mutant sequences while MS only detected one sequence.

Figure 6 Unextended primers (UEP) and extended primers (EP)

| | nt Site | Direction | Concentration (µM) | UEP Sequence | SEQ ID NO | UEP MW (Da) | EP 1 (Call) | EP1 MW (Da) | EP 2 | EP 2 MW | EP 3 | EP 3 MW | EP 4 | EP 4 MW |
|---|---|---|---|---|---|---|---|---|---|---|---|---|---|---|
| Assay 1 | nt_646 | R | 8 | AAACGGACTGAGGCCCA | 5 | 5213.4 | G | 5460.6 | T | 5484.6 | C | 5500.6 | | |
| | nt_404 | R | 8 | TAGCAGCAGGATGAAGA | 6 | 5292.5 | T | 5563.7 | C | 5579.7 | | | | |
| | nt_671 | R | 8 | ATGGCACTAGTAAACTGA | 7 | 5531.6 | T | 5802.8 | C | 5818.8 | | | | |
| | nt_341 | F | 8 | gcCCTCCAATCACTCACCA | 8 | 5637.7 | C | 5884.9 | A | 5908.9 | | | | |
| | nt_750 | R | 8 | CAGACTTGGCCCCAATAC | 9 | 5717.7 | G | 5964.9 | T | 5988.9 | C | 6004.9 | A | 6044.8 |
| | nt_527 | R | 8 | TTGCCTTGAGCAGGTGTCG | 10 | 5850.8 | T | 6122 | A | 6177.9 | | | | |
| | nt_367 | R | 8 | CGCAGACACATCCAGCGATA | 11 | 6080 | G | 6327.2 | T | 6351.2 | C | 6367.2 | A | 6407.1 |
| | nt_871 | R | 10 | CAATTACGTAGACCATGAAGT | 12 | 6438.2 | C | 6725.4 | A | 6765.3 | | | | |
| | nt_728 | F | 10 | ccacaTTTCCCCCACTGTTTGG | 13 | 6597.3 | C | 6844.5 | A | 6924.4 | | | | |
| | nt_796 | R | 10 | tAGACAAAAGAAAATTGGTAATAG | 14 | 7465.9 | G | 7713.1 | T | 7737.1 | | | | |
| | nt_373 | R | 10 | gGATAAAACGCCGCAGACACATCCA | 15 | 7638 | C | 7925.2 | A | 7965.1 | | | | |
| | nt_863 | R | 16 | gACGTAGACCATGAAGTTTAGGGAA | 16 | 7779.1 | C | 8066.3 | A | 8106.2 | | | | |
| Assay 2 | nt_665 | F | 8 | GCCTCAGTCCGTTTC | 17 | 4494.9 | C | 4742.1 | T | 4822 | | | | |
| | nt_659 | F | 8 | GAGTGGGCCTCAGTC | 18 | 4609 | C | 4856.2 | T | 4936.1 | | | | |
| | nt_533 | R | 8 | cAGTTGCCTTGAGCAG | 19 | 4897.2 | G | 5144.4 | C | 5184.4 | | | | |
| | nt_886 | R | 7 | TCCCCAACTTCCAATTA | 20 | 5049.3 | G | 5296.5 | A | 5376.4 | | | | |
| | nt_748 | R | 7 | acTGGCCCCAATACCA | 21 | 5084.3 | G | 5331.5 | A | 5411.4 | | | | |
| | nt_700 | R | 10 | GGGGAAAGCCCTACGAA | 22 | 5253.4 | G | 5500.6 | A | 5580.5 | | | | |
| | nt_667 | F | 8 | cccCCTCAGTCCGTTTCTC | 23 | 5626.7 | C | 5873.8 | A | 5897.9 | T | 5953.7 | | |
| | nt_1899 | F | 8 | cTAAGGGTCAATGTCCATG | 24 | 5827.8 | G | 6075 | A | 6154.9 | | | | |
| | nt_841 | R | 8 | ACCCCATCTTTTTGTTTAT | 25 | 5998.9 | G | 6246.1 | C | 6286.1 | A | 6326 | | |
| | nt_382 | F | 10 | acgGGTTATCGCTGGATGTG | 26 | 6204 | G | 6491.2 | T | 6531.1 | | | | |
| | nt_361 | F | 8 | ccaaCTCCGTCCTCCAATTTG | 27 | 6581.3 | A | 6852.5 | C | 6908.4 | | | | |
| | nt_512 | F | 10 | gataAACAACAACCAGTACGGGA | 28 | 7083.6 | C | 7330.8 | A | 7354.9 | | | | |
| | nt_734 | F | 10 | cttgCCCCACTGTTTGGCTTTCA | 29 | 7221.7 | G | 7508.9 | T | 7548.8 | | | | |
| | nt_836 | F | 10 | aTTTTGTCTCTGGGTATACATTTAA | 30 | 7652 | C | 7899.2 | A | 7923.2 | | | | |
| | nt_680 | R | 10 | ggggACCACTGAACAAATGGCACTA | 31 | 7709 | G | 7956.2 | C | 7996.2 | | | | |
| | nt_766 | R | 16 | tggggAGGGACTCACGATGTGTACAG | 32 | 8420.5 | T | 8691.7 | A | 8747.6 | | | | |

Figure 6 (continued)

| | nt Site | Direction | Concentration (μM) | UEP Sequence | SEQ ID NO | UEP MW (Da) | EP 1 (Call) | EP1 MW (Da) | EP 2 | EP 2 MW | EP 3 | EP 3 MW | EP 4 | EP 4 MW |
|---|---|---|---|---|---|---|---|---|---|---|---|---|---|---|
| | nt_1764 | R | 18 | gggttCCTACAGCCTCCTAATACAAAGA | 33 | 8541.6 | G | 8788.8 | A | 8868.7 | | | | |
| Assay 3 | nt_616 | R | 8 | TGCGAAAGCCCAGGA | 34 | 4611 | G | 4858.2 | A | 4938.1 | | | | |
| | nt_1613 | R | 8 | GGGCGTTCACGGTGGT | 35 | 4969.2 | G | 5216.4 | A | 5296.3 | | | | |
| | nt_532 | F | 8 | ttCAAAACCTGCACGAC | 36 | 5123.4 | A | 5394.6 | T | 5450.5 | | | | |
| | nt_1858 | F | 7 | TCATCTCTTGTACATGTCC | 37 | 5704.7 | C | 5951.9 | T | 6031.8 | | | | |
| | nt_670 | F | 7 | ctTCAGTCCGTTTCTCTTG | 38 | 5711.7 | A | 5982.9 | G | 5998.9 | | | | |
| | nt_337 | F | 8 | TCCCCAACCTCCAATCACTC | 39 | 5901.9 | G | 6173.1 | T | 6229 | | | | |
| | nt_679 | R | 10 | CACTGAACAAATGGCACTAG | 40 | 6119 | C | 6366.2 | A | 6446.1 | | | | |
| | nt_843 | F | 10 | GGGTATACATTAAACCCTAA | 41 | 6413.2 | C | 6660.4 | T | 6740.3 | | | | |
| | nt_379 | F | 10 | ggggCCTGGTTATCGCTGGAT | 42 | 6509.2 | A | 6780.4 | G | 6796.4 | | | | |
| | nt_832 | F | 10 | TCTTTTGTCTCTGGGTATACAT | 43 | 6697.4 | C | 6944.5 | A | 6968.6 | T | 7024.5 | | |
| | nt_770 | F | 10 | aggggATTGGGGGCCAAGTCTG | 44 | 6896.5 | C | 7143.7 | T | 7223.6 | | | | |
| | nt_791 | R | 14 | AAAGAAAATTGGTAATAGAGGTA | 45 | 7192.7 | T | 7463.9 | A | 7519.8 | | | | |
| | nt_831 | F | 14 | ctTgCTTTTGTCTCTGGGTATACA | 46 | 7315.8 | A | 7587 | G | 7603 | T | 7642.8 | | |
| | nt_826 | F | 14 | aacccATTTCTTCTTTTGTCTCTGGGT | 47 | 7555.9 | A | 7827.1 | G | 7843.1 | | | | |
| | nt_385 | F | 14 | ttccgGGTTATCGCTGGATGTGTCT | 48 | 7686 | C | 7933.2 | G | 7973.2 | | | | |
| | nt_799 | R | 14 | ctaAGAGACAAAAGAAAATTGGTAA | 49 | 7764.1 | G | 8011.3 | A | 8091.2 | | | | |
| | nt_839 | F | 14 | ccttgCTCTGGGTATACATTTAAACC | 50 | 7896.1 | C | 8143.3 | A | 8167.4 | | | | |
| Assay 4 | nt_1896 | F | 8 | GCCTTGGGTGGCTTT | 51 | 4606 | A | 4877.2 | G | 4893.2 | | | | |
| | nt_895 | R | 8 | GGCAATGTTCCCCAAC | 52 | 4826.2 | G | 5073.3 | T | 5097.4 | A | 5153.3 | | |
| | nt_709 | F | 8 | TTCAGTGGTTCGTAGG | 53 | 4943.2 | A | 5214.4 | G | 5230.4 | | | | |
| | nt_772 | F | 10 | TGGGGGCCAAGTCTGTA | 54 | 5266.4 | C | 5513.6 | T | 5593.5 | | | | |
| | nt_400 | F | 8 | TCTGCGGCGTTTTATCAT | 55 | 5471.6 | A | 5718.7 | T | 5742.8 | | | | |
| | nt_635 | F | 8 | gaaTGGGCTTTCGCAAAA | 56 | 5547.6 | C | 5794.8 | T | 5874.7 | | | | |
| | nt_625 | F | 8 | ccacCCCATCATCCTGGGC | 57 | 5669.7 | C | 5916.9 | T | 5996.8 | | | | |
| | nt_741 | R | 8 | taCCCCAATACCACATCATC | 58 | 5949.9 | G | 6197.1 | T | 6221.1 | C | 6237.1 | | |
| | nt_739 | F | 10 | ACTGTTTGGCTTTCAGCTAT | 59 | 6089 | A | 6360.2 | G | 6376.2 | | | | |
| | nt_773 | F | 10 | gtttGGGGCCAAGTCTGTAC | 60 | 6164 | C | 6411.2 | A | 6435.2 | G | 6451.2 | | |
| | nt_1762 | F | 14 | GGGGGAGGAGATTAGGTTAA | 61 | 6326.1 | A | 6597.3 | T | 6653.2 | | | | |
| | nt_740 | R | 10 | gtCCCCCAATACCACATCATCC | 62 | 6544.3 | G | 6791.5 | T | 6815.5 | | | | |
| | nt_814 | R | 14 | TTTAAATGTATACCAGAGACA | 63 | 6726.4 | T | 6973.6 | T | 6997.6 | A | 7053.5 | | |
| | nt_877 | F | 16 | agacGGGGTTATTCCCTAAACTTC | 64 | 6940.5 | A | 7211.7 | G | 7227.7 | | | | |

US 8,435,764 B2

```
                         SEQUENCE LISTING

<160> NUMBER OF SEQ ID NOS: 200

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
gttggatgga ctcgtggtgg acttctctca                                    30

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ggatgcccac aattckttga catactttcc                                    30

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
acgttggatg acctctgcac gtyrcatgga                                    30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
ggatggagag taactccaca gtagctccaa                                    30

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
aaacggactg aggccca                                                  17

<210> SEQ ID NO 6
<211> LENGTH: 17
<212> TYPE: DNA
<213> ORGANISM: Artificial
<220> FEATURE:
<223> OTHER INFORMATION: primer

<400> SEQUENCE: 6
```

```
tagcagcagg atgaaga                                              17

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
atggcactag taaactga                                             18

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
gccctccaat cactcacca                                            19

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
cagacttggc ccccaatac                                            19

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10 ttgcccttgag caggtgtcg                                           19

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
cgcagacaca tccagcgata                                           20

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
caattacgta gaccatgaag t                                         21

<210> SEQ ID NO 13
<211> LENGTH: 22
<212> TYPE: DNA
<213> ORGANISM: Artificial
<220> FEATURE:
```

<223> OTHER INFORMATION: primer

<400> SEQUENCE: 13
ccacatttcc cccactgttt gg                                          22

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
tagacaaaag aaaattggta atag                                        24

<210> SEQ ID NO 15
<211> LENGTH: 25
<212> TYPE: DNA
<213> ORGANISM: Artificial
<220> FEATURE:
<223> OTHER INFORMATION: primer

<400> SEQUENCE: 15
ggataaaacg ccgcagacac atcca                                       25

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
gacgtagacc atgaagttta gggaa                                       25

<210> SEQ ID NO 17
<211> LENGTH: 15
<212> TYPE: DNA
<213> ORGANISM: Artificial
<220> FEATURE:
<223> OTHER INFORMATION: primer

<400> SEQUENCE: 17
gcctcagtcc gtttc                                                  15

<210> SEQ ID NO 18
<211> LENGTH: 15
<212> TYPE: DNA
<213> ORGANISM: Artificial
<220> FEATURE:
<223> OTHER INFORMATION: primer

<400> SEQUENCE: 18
gagtgggcct cagtc                                                  15

<210> SEQ ID NO 19
<211> LENGTH: 16
<212> TYPE: DNA
<213> ORGANISM: Artificial
<220> FEATURE:
<223> OTHER INFORMATION: primer

<400> SEQUENCE: 19
cagttgcctt gagcag                                                 16

<210> SEQ ID NO 20

```
<211> LENGTH: 17
<212> TYPE: DNA
<213> ORGANISM: Artificial
<220> FEATURE:
<223> OTHER INFORMATION: primer

<400> SEQUENCE: 20
tccccaactt ccaatta                                                   17

<210> SEQ ID NO 21
<211> LENGTH: 17
<212> TYPE: DNA
<213> ORGANISM: Artificial
<220> FEATURE:
<223> OTHER INFORMATION: primer

<400> SEQUENCE: 21
actggccccc aatacca                                                   17

<210> SEQ ID NO 22
<211> LENGTH: 17
<212> TYPE: DNA
<213> ORGANISM: Artificial
<220> FEATURE:
<223> OTHER INFORMATION: primer

<400> SEQUENCE: 22
ggggaaagcc ctacgaa                                                   17

<210> SEQ ID NO 23
<211> LENGTH: 19
<212> TYPE: DNA
<213> ORGANISM: Artificial
<220> FEATURE:
<223> OTHER INFORMATION: primer

<400> SEQUENCE: 23
ccccctcagt ccgtttctc                                                 19

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
ctaagggtca atgtccatg                                                 19

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
accccatctt tttgttttat                                                20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
```

```
acgggttatc gctggatgtg                                                20

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
ccaactcctg tcctccaatt tg                                             22

<210> SEQ ID NO 28
<211> LENGTH: 23
<212> TYPE: DNA
<213> ORGANISM: Artificial
<220> FEATURE:
<223> OTHER INFORMATION: primer

<400> SEQUENCE: 28
gataaacaac aaccagtacg gga                                            23

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
cttgccccca ctgtttggct ttca                                           24

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
attttgtctc tgggtataca tttaa                                          25

<210> SEQ ID NO 31
<211> LENGTH: 25
<212> TYPE: DNA
<213> ORGANISM: Artificial
<220> FEATURE:
<223> OTHER INFORMATION: primer

<400> SEQUENCE: 31
ggggaccact gaacaaatgg cacta                                          25

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32
tggggaggga ctcacgatgt tgtacag                                        27

<210> SEQ ID NO 33
<211> LENGTH: 28
<212> TYPE: DNA
<213> ORGANISM: Artificial
<220> FEATURE:
```

<223> OTHER INFORMATION: primer

<400> SEQUENCE: 33
gggttcctac agcctcctaa tacaaaga                                28

<210> SEQ ID NO 34
<211> LENGTH: 15
<212> TYPE: DNA
<213> ORGANISM: Artificial
<220> FEATURE:
<223> OTHER INFORMATION: primer

<400> SEQUENCE: 34
tgcgaaagcc cagga                                              15

<210> SEQ ID NO 35
<211> LENGTH: 16
<212> TYPE: DNA
<213> ORGANISM: Artificial
<220> FEATURE:
<223> OTHER INFORMATION: primer

<400> SEQUENCE: 35
gggcgttcac ggtggt                                             16

<210> SEQ ID NO 36
<211> LENGTH: 17
<212> TYPE: DNA
<213> ORGANISM: Artificial
<220> FEATURE:
<223> OTHER INFORMATION: primer

<400> SEQUENCE: 36
ttcaaaacct gcacgac                                            17

<210> SEQ ID NO 37
<211> LENGTH: 19
<212> TYPE: DNA
<213> ORGANISM: Artificial
<220> FEATURE:
<223> OTHER INFORMATION: primer

<400> SEQUENCE: 37
tcatctcttg tacatgtcc                                          19

<210> SEQ ID NO 38
<211> LENGTH: 19
<212> TYPE: DNA
<213> ORGANISM: Artificial
<220> FEATURE:
<223> OTHER INFORMATION: primer

<400> SEQUENCE: 38
cttcagtccg tttctcttg                                          19

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
tccccaacct ccaatcactc                                         20

<210> SEQ ID NO 40

```
<211> LENGTH: 20
<212> TYPE: DNA
<213> ORGANISM: Artificial
<220> FEATURE:
<223> OTHER INFORMATION: primer

<400> SEQUENCE: 40
cactgaacaa atggcactag                                              20

<210> SEQ ID NO 41
<211> LENGTH: 21
<212> TYPE: DNA
<213> ORGANISM: Artificial
<220> FEATURE:
<223> OTHER INFORMATION: primer

<400> SEQUENCE: 41
gggtatacat ttaaaccota a                                            21

<210> SEQ ID NO 42
<211> LENGTH: 21
<212> TYPE: DNA
<213> ORGANISM: Artificial
<220> FEATURE:
<223> OTHER INFORMATION: primer

<400> SEQUENCE: 42
ggggcctggt tatcgctgga t                                            21

<210> SEQ ID NO 43
<211> LENGTH: 22
<212> TYPE: DNA
<213> ORGANISM: Artificial
<220> FEATURE:
<223> OTHER INFORMATION: primer

<400> SEQUENCE: 43
tcttttgtct ctgggtatac at                                           22

<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
aggggattgg gggccaagtc tg                                           22

<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
aaagaaaatt ggtaatagag gta                                          23

<210> SEQ ID NO 46
<211> LENGTH: 24
<212> TYPE: DNA
<213> ORGANISM: Artificial
<220> FEATURE:
<223> OTHER INFORMATION: primer

<400> SEQUENCE: 46
```

```
cttgcttttg tctctgggta taca                                          24
```

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47

```
accccatttt cttttgtctc tgggt                                         25
```

<210> SEQ ID NO 48
<211> LENGTH: 25
<212> TYPE: DNA
<213> ORGANISM: Artificial
<220> FEATURE:
<223> OTHER INFORMATION: primer

<400> SEQUENCE: 48

```
ttccgggtta tcgctggatg tgtct                                         25
```

<210> SEQ ID NO 49
<211> LENGTH: 25
<212> TYPE: DNA
<213> ORGANISM: Artificial
<220> FEATURE:
<223> OTHER INFORMATION: primer

<400> SEQUENCE: 49

```
ctaagagaca aagaaaatt ggtaa                                          25
```

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50

```
ccttgctctg ggtatacatt taaacc                                        26
```

<210> SEQ ID NO 51
<211> LENGTH: 15
<212> TYPE: DNA
<213> ORGANISM: Artificial
<220> FEATURE:
<223> OTHER INFORMATION: primer

<400> SEQUENCE: 51

```
gccttgggtg gcttt                                                    15
```

<210> SEQ ID NO 52
<211> LENGTH: 16
<212> TYPE: DNA
<213> ORGANISM: Artificial
<220> FEATURE:
<223> OTHER INFORMATION: primer

<400> SEQUENCE: 52

```
ggcaatgttc cccaac                                                   16
```

<210> SEQ ID NO 53
<211> LENGTH: 16
<212> TYPE: DNA
<213> ORGANISM: Artificial
<220> FEATURE:

<223> OTHER INFORMATION: primer

<400> SEQUENCE: 53
ttcagtggtt cgtagg                                                    16

<210> SEQ ID NO 54
<211> LENGTH: 17
<212> TYPE: DNA
<213> ORGANISM: Artificial
<220> FEATURE:
<223> OTHER INFORMATION: primer

<400> SEQUENCE: 54
tgggggccaa gtctgta                                                   17

<210> SEQ ID NO 55
<211> LENGTH: 18
<212> TYPE: DNA
<213> ORGANISM: Artificial
<220> FEATURE:
<223> OTHER INFORMATION: primer

<400> SEQUENCE: 55
tctgcggcgt tttatcat                                                  18

<210> SEQ ID NO 56
<211> LENGTH: 18
<212> TYPE: DNA
<213> ORGANISM: Artificial
<220> FEATURE:
<223> OTHER INFORMATION: primer

<400> SEQUENCE: 56
gaatgggctt tcgcaaaa                                                  18

<210> SEQ ID NO 57
<211> LENGTH: 19
<212> TYPE: DNA
<213> ORGANISM: Artificial
<220> FEATURE:
<223> OTHER INFORMATION: primer

<400> SEQUENCE: 57
ccaccccatc atcctgggc                                                 19

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
taccccaata ccacatcatc                                                20

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
actgtttggc tttcagctat                                                20

<210> SEQ ID NO 60

```
<211> LENGTH: 20
<212> TYPE: DNA
<213> ORGANISM: Artificial
<220> FEATURE:
<223> OTHER INFORMATION: primer

<400> SEQUENCE: 60
gtttggggcc aagtctgtac                                              20

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
gggggaggag attaggttaa                                              20

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
gtcccccaat accacatcat cc                                           22

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
tttaaatgta tacccagaga ca                                           22

<210> SEQ ID NO 64
<211> LENGTH: 24
<212> TYPE: DNA
<213> ORGANISM: Artificial
<220> FEATURE:
<223> OTHER INFORMATION: primer

<400> SEQUENCE: 64
agacggggtt attccctaaa cttc                                         24

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
gttggatgga ctcgtggtgg acttctctca                                   30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
```

-continued

```
ggatggagag taactccaca gtagctccaa                                    30
```

<210> SEQ ID NO 67
<211> LENGTH: 22
<212> TYPE: DNA
<213> ORGANISM: Artificial
<220> FEATURE:
<223> OTHER INFORMATION: primer

<400> SEQUENCE: 67

```
gygccatttg ttcagtggtt cg                                            22
```

<210> SEQ ID NO 68
<211> LENGTH: 24
<212> TYPE: DNA
<213> ORGANISM: Artificial
<220> FEATURE:
<223> OTHER INFORMATION: primer

<400> SEQUENCE: 68

```
aaacatagag gttccttgag cagg                                          24
```

<210> SEQ ID NO 69
<211> LENGTH: 109
<212> TYPE: DNA
<213> ORGANISM: Hepatitis B virus

<400> SEQUENCE: 69

```
cccctgctcg tgttacaggc ggggttttc ttgttgacaa gaatcctcac aataccgcag    60
agtctagact cgtggtggac ttctctcaat tttctagggg ggaccaccg              109
```

<210> SEQ ID NO 70
<211> LENGTH: 109
<212> TYPE: DNA
<213> ORGANISM: Hepatitis B virus

<400> SEQUENCE: 70

```
cccctgctcg tgttacaggc ggggttttc ttgttgacaa gaatcctcac aataccgcag    60
agtctagact cgtggtggac ttctctcaat tttctagggg ggaccaccg              109
```

<210> SEQ ID NO 71
<211> LENGTH: 109
<212> TYPE: DNA
<213> ORGANISM: Hepatitis B virus

<400> SEQUENCE: 71

```
cccctgctcg tgttacaggc ggggttttc ttgttgacaa gaatcctcac aataccgcag    60
agtctagact cgtggtggac ttctctcaat tttctagggg gaactaccg              109
```

<210> SEQ ID NO 72
<211> LENGTH: 109
<212> TYPE: DNA
<213> ORGANISM: Hepatitis B virus

<400> SEQUENCE: 72

```
cccctgctcg tgttacaggc ggggttttc ttgttgacaa gaatcctcac aataccgcag    60
agtctagact cgtggtggac ttctctcaat tttctagggg gaactaccg              109
```

<210> SEQ ID NO 73
<211> LENGTH: 109
<212> TYPE: DNA
<213> ORGANISM: Hepatitis B virus

<400> SEQUENCE: 73
cccctgctcg tgttacaggc ggggttttc ttgttgacaa aaatcctcac aataccgcag    60
agtctagact cgtggtggac ttctctcaat tttctagggg gagctcccg              109

<210> SEQ ID NO 74
<211> LENGTH: 109
<212> TYPE: DNA
<213> ORGANISM: Hepatitis B virus

<400> SEQUENCE: 74
cccctgctcg tgttacaggc ggggtgtttc ttgttgacaa aaatcctcac aataccgcag    60
agtctagact cgtggtggac ttctctcaat tttctagggg gagctcccg              109

<210> SEQ ID NO 75
<211> LENGTH: 109
<212> TYPE: DNA
<213> ORGANISM: Hepatitis B virus

<400> SEQUENCE: 75
cccctgctcg tgttacaggc ggggttttc ttgttgacaa aaatcctcac aataccacag    60
agtctagact cgtggtggac ttctctcaat tttctagggg gaacacccg              109

<210> SEQ ID NO 76
<211> LENGTH: 109
<212> TYPE: DNA
<213> ORGANISM: Hepatitis B virus

<400> SEQUENCE: 76
cccctgctcg tgttacaggc ggggttttc ttgttgacaa aaatcctcac aataccacag    60
agtctagact cgtggtggac ttctctcaat tttctagggg aaacacccg              109

<210> SEQ ID NO 77
<211> LENGTH: 109
<212> TYPE: DNA
<213> ORGANISM: Hepatitis B virus

<400> SEQUENCE: 77
cccctgctcg tgttacaggc ggggttttc ttgttgacaa aaatcctcac aataccacag    60
agtctagact cgtggtggac ttctctcagt tttctagggg gaacacccg              109

<210> SEQ ID NO 78
<211> LENGTH: 109
<212> TYPE: DNA
<213> ORGANISM: Hepatitis B virus

<400> SEQUENCE: 78
cccctgctcg tgttacaggc ggggttttc ttgttgacaa aaatcctcac aataccacag    60
agtctagact cgtggtggac ttctctcaat tttctagggg gaacacccg              109

<210> SEQ ID NO 79
<211> LENGTH: 109
<212> TYPE: DNA
<213> ORGANISM: Hepatitis B virus

<400> SEQUENCE: 79
cccctgctcg tgttacaggc ggggttttc ttgttgacaa aaatcctcac aataccacag    60
agtctagact cgtggtggac ttctctcaat tttctagggg gaacacccg              109

<210> SEQ ID NO 80

-continued

<210> SEQ ID NO 80
<211> LENGTH: 109
<212> TYPE: DNA
<213> ORGANISM: Hepatitis B virus

<400> SEQUENCE: 80
cccctgcttg tgttacaggc ggggttttc ttgttgacaa aaatcctcac aataccacag      60
agtctagact cgtggtggac ttctctcaat tttctagggg gaacacccg                 109

<210> SEQ ID NO 81
<211> LENGTH: 109
<212> TYPE: DNA
<213> ORGANISM: Hepatitis B virus

<400> SEQUENCE: 81
cccctgctcg tgttacaggc ggggttttc tcgttgacaa aaatcctcac aataccacag      60
agtctagact cgtggtggac ttctctcaat tttctagggg aaacacccg                 109

<210> SEQ ID NO 82
<211> LENGTH: 109
<212> TYPE: DNA
<213> ORGANISM: Hepatitis B virus

<400> SEQUENCE: 82
cccctgctcg tgttacaggc ggggttttc ttgttgacaa aaatcctcac aataccacag      60
agtctagact cgtggtggac ttctctcaat tttctagggg gaacacccg                 109

<210> SEQ ID NO 83
<211> LENGTH: 109
<212> TYPE: DNA
<213> ORGANISM: Hepatitis B virus

<400> SEQUENCE: 83
cccctgctcg tgttacaggc ggggttttc ttgttgacaa aaatcctcac aataccacag      60
agtctagact cgtggtggac ttctctcaat tttctagggg gaacacccg                 109

<210> SEQ ID NO 84
<211> LENGTH: 109
<212> TYPE: DNA
<213> ORGANISM: Hepatitis B virus

<400> SEQUENCE: 84
cccctgctcg tgttacaggc ggggttttc tcgttgacaa aaatcctcac aataccacag      60
agtctagact cgtggtggac ttctctcaat tttctagggg gaacacccg                 109

<210> SEQ ID NO 85
<211> LENGTH: 109
<212> TYPE: DNA
<213> ORGANISM: Hepatitis B virus

<400> SEQUENCE: 85
cccctgctcg tgttacaggc ggggttttc ttgttgacaa gaatcctcac aataccacag      60
agtctagact cgtggtggac ttctctcaat tttctagggg gagcaccca                 109

<210> SEQ ID NO 86
<211> LENGTH: 109
<212> TYPE: DNA
<213> ORGANISM: Hepatitis B virus

<400> SEQUENCE: 86
cccctgctcg tgttacaggc ggggttttc ttgttgacaa gaatcctcac aataccacag      60

```
agtctagact cgtggtggac ttctctcaat tttctagggg gagcacccg        109

<210> SEQ ID NO 87
<211> LENGTH: 109
<212> TYPE: DNA
<213> ORGANISM: Hepatitis B virus

<400> SEQUENCE: 87
cccctgctcg tgttacaggc ggggttttc ttgttgacaa gaatcctcac aataccacag    60
agtctagact cgtggtggac ttctctcaat tttctagggg gagcaccca        109

<210> SEQ ID NO 88
<211> LENGTH: 109
<212> TYPE: DNA
<213> ORGANISM: Hepatitis B virus

<400> SEQUENCE: 88
cccctgctcg tgttacaggc ggggttttc ttgttgacaa gaatcctcac aataccacag    60
agtctagact cgtggtggac ttctctcaat tttctagggg gagcaccca        109

<210> SEQ ID NO 89
<211> LENGTH: 109
<212> TYPE: DNA
<213> ORGANISM: Hepatitis B virus

<400> SEQUENCE: 89
cccctgctcg tgttacaggc ggggttttc ttgttgacaa aaatcctcac aataccacag    60
agtctagact cgtggtggac ttctctcaat tttctagggg gagcaccca        109

<210> SEQ ID NO 90
<211> LENGTH: 109
<212> TYPE: DNA
<213> ORGANISM: Hepatitis B virus

<400> SEQUENCE: 90
cccctgctcg tgttacaggc ggggttttc ttgttgacaa aaatcctcac aataccacag    60
agtctcgact cgtggtggac ttctctcaat tttctagggg gagcaccca        109

<210> SEQ ID NO 91
<211> LENGTH: 109
<212> TYPE: DNA
<213> ORGANISM: Hepatitis B virus

<400> SEQUENCE: 91
cccctgctcg tgttacaggc ggggttttc ttgttgacaa gaatcctcac aataccacag    60
agtctagact cgtggtggac ttctctcaat tttctagggg gagcaccca        109

<210> SEQ ID NO 92
<211> LENGTH: 109
<212> TYPE: DNA
<213> ORGANISM: Hepatitis B virus

<400> SEQUENCE: 92
cccctgctcg tgttacaggc ggggttttc ttgttgacaa gaatcctcac aataccacag    60
agtctagact cgtggtggac ttctctcaat tttctagggg gagcaccca        109

<210> SEQ ID NO 93
<211> LENGTH: 109
<212> TYPE: DNA
<213> ORGANISM: Hepatitis B virus
```

```
<400> SEQUENCE: 93
cccctgctcg tgttacaggc ggggttttc  ttgttgacaa gaatcctcac aataccacag      60
agtctagact cgtggtggac ttctctcaat tttctagggg gagcaccca                  109

<210> SEQ ID NO 94
<211> LENGTH: 109
<212> TYPE: DNA
<213> ORGANISM: Hepatitis B virus

<400> SEQUENCE: 94
cccctgctcg tgttacaggc ggggttttc  ttgttgacaa gaatcctcac aataccgcag      60
agtctagact cgtggtggac ttctctcaat tttctagggg gatcacccg                  109

<210> SEQ ID NO 95
<211> LENGTH: 109
<212> TYPE: DNA
<213> ORGANISM: Hepatitis B virus

<400> SEQUENCE: 95
cccctgctcg tgttacaggc ggggttttc  ttgttgacaa gaatcctcac aataccgcag      60
agtctagact cgtggtggac ttctctcaat tttctagggg gatcacccg                  109

<210> SEQ ID NO 96
<211> LENGTH: 109
<212> TYPE: DNA
<213> ORGANISM: Hepatitis B virus

<400> SEQUENCE: 96
cccctgctcg tgttacaggc ggggttttc  ttgttgacaa gaatcctcac aataccgcag      60
agtctagact cgtggtggac ttctctcaat tttctagggg gatcacccg                  109

<210> SEQ ID NO 97
<211> LENGTH: 109
<212> TYPE: DNA
<213> ORGANISM: Hepatitis B virus

<400> SEQUENCE: 97
cccctgctcg tgttacaggc ggtgtgtttc ttgttgacaa aaatcctcac aataccacag      60
agtctagact cgtggtggac ttctctcaat tttctagggg gactacccg                  109

<210> SEQ ID NO 98
<211> LENGTH: 109
<212> TYPE: DNA
<213> ORGANISM: Hepatitis B virus

<400> SEQUENCE: 98
cccctgctcg tgttacaggc ggtgtgtttc ttgttgacaa aaatcctcac aataccacag      60
agtctagact cgtggtggac ttctctcaat tttctagggg gactacccg                  109

<210> SEQ ID NO 99
<211> LENGTH: 109
<212> TYPE: DNA
<213> ORGANISM: Hepatitis B virus

<400> SEQUENCE: 99
cccctgctcg tgttacaggc ggtgttttcc ttgttgacaa aaatcctcac aataccacag      60
agtctagact cgtggtggac ttctctcaat tttctagggg gaacaaccg                  109

<210> SEQ ID NO 100
```

```
<211> LENGTH: 109
<212> TYPE: DNA
<213> ORGANISM: Hepatitis B virus

<400> SEQUENCE: 100 cccttctcg tgttacaggc ggtgtgtttc ttgttgacaa aaatcctcac ataccacgg        60 agtctagact cgtggtggac ttctctcaat tttctagggg taccacccg                 109

<210> SEQ ID NO 101
<211> LENGTH: 22
<212> TYPE: DNA
<213> ORGANISM: Artificial
<220> FEATURE:
<223> OTHER INFORMATION: 251F primer

<400> SEQUENCE: 101
gactcgtggt ggacttctct ca                                              22

<210> SEQ ID NO 102
<211> LENGTH: 105
<212> TYPE: DNA
<213> ORGANISM: Hepatitis B virus

<400> SEQUENCE: 102
tcaaagaatg ttttagaaaa cttcctgtta acaggcctat tgattggaaa gtctgtcaac     60
gtattgtggg tcttttgggt tttgctgctc cttttacaca atgtg                     105

<210> SEQ ID NO 103
<211> LENGTH: 105
<212> TYPE: DNA
<213> ORGANISM: Hepatitis B virus

<400> SEQUENCE: 103
tcaaagaatg ttttagaaaa cttcctgtta acaggcctat tgattggaaa gtctgtcaac     60
gtattgtggg tcttttgggt tttgctgctc cttttacaca atgtg                     105

<210> SEQ ID NO 104
<211> LENGTH: 105
<212> TYPE: DNA
<213> ORGANISM: Hepatitis B virus

<400> SEQUENCE: 104
tcaaagaatg ttttagaaaa cttcctgtta acaggcctat tgattggaaa gtctgtcaac     60
gtattgtggg tcttttgggt tttgctgccc cttttacaca atgtg                     105

<210> SEQ ID NO 105
<211> LENGTH: 105
<212> TYPE: DNA
<213> ORGANISM: Hepatitis B virus

<400> SEQUENCE: 105
tcaaagaatg ctttagaaaa cttcctgtta acaggcctat tgattggaaa gtctgtcaac     60
gtattgtggg tcttttgggt tttgctgccc cttttacaca atgtg                     105

<210> SEQ ID NO 106
<211> LENGTH: 105
<212> TYPE: DNA
<213> ORGANISM: Hepatitis B virus

<400> SEQUENCE: 106
tcaaaatgtg ttttaggaaa cttcctgtaa acaggcctat tgattggaaa gtatgtcaac     60
```

-continued

```
gaattgtggg tcttttgggg tttgccgccc ctttcacgca atgtg          105
```

<210> SEQ ID NO 107
<211> LENGTH: 105
<212> TYPE: DNA
<213> ORGANISM: Hepatitis B virus

<400> SEQUENCE: 107

```
tcaaaatgtg ttttagaaaa cttcctgtaa acaggcctat tgattggaaa gtatgtcaac    60
gaattgtggg tcttttgggg tttgccgccc ctttcacgca atgtg                   105
```

<210> SEQ ID NO 108
<211> LENGTH: 105
<212> TYPE: DNA
<213> ORGANISM: Hepatitis B virus

<400> SEQUENCE: 108

```
tcaaaatgtg ttttaggaaa cttcctgtaa acaggcctat tgattggaaa gtatgtcaac    60
gaattgtggg tcttttgggg tttgccgccc ctttcacgca atgtg                   105
```

<210> SEQ ID NO 109
<211> LENGTH: 105
<212> TYPE: DNA
<213> ORGANISM: Hepatitis B virus

<400> SEQUENCE: 109

```
tcaaaatgtg ttttaggaaa cttcctgtaa acaggccaat tgattggaaa gtatgtcaac    60
gaattgtggg tcttttgggg tttgccgccc cttttacgca atgtg                   105
```

<210> SEQ ID NO 110
<211> LENGTH: 105
<212> TYPE: DNA
<213> ORGANISM: Hepatitis B virus

<400> SEQUENCE: 110

```
tcaaaaggtg ttttaggaaa cttcctgtaa acaggccaat tgattggaaa gtatgtcaac    60
gaattgtggg tcttttgggg tttgccgccc ctttcacgca atgtg                   105
```

<210> SEQ ID NO 111
<211> LENGTH: 105
<212> TYPE: DNA
<213> ORGANISM: Hepatitis B virus

<400> SEQUENCE: 111

```
tcaaactgtg ttttaggaaa cttcctgtaa acaggcctat tgattggaaa gtatgtcaac    60
gaattgtggg tcttttgggg tttgccgccc ctttcacaca atgtg                   105
```

<210> SEQ ID NO 112
<211> LENGTH: 105
<212> TYPE: DNA
<213> ORGANISM: Hepatitis B virus

<400> SEQUENCE: 112

```
tcaaaatgtg ttttagaaaa cttcctgtaa acaggcctat tgattggaaa gtatgtcaac    60
gaattgtggg tcttttgggg tttgccgccc cttttacgca atgtg                   105
```

<210> SEQ ID NO 113
<211> LENGTH: 105
<212> TYPE: DNA
<213> ORGANISM: Hepatitis B virus

```
<400> SEQUENCE: 113
tcaaaatgtg ttttaggaaa cttcctgcaa acagacctat tgattggaaa gtgtgtcaac    60
gaattgtggg tcttttgggg tttgccgccc ctttcacgca atgtg                   105

<210> SEQ ID NO 114
<211> LENGTH: 105
<212> TYPE: DNA
<213> ORGANISM: Hepatitis B virus

<400> SEQUENCE: 114
tcaaacactg tttagaaaaa cttcctgtta acaggcctat tgattggaaa gtatgtcaaa    60
gaattgtggg tcttttgggc tttgctgctc catttacaca atgtg                   105

<210> SEQ ID NO 115
<211> LENGTH: 105
<212> TYPE: DNA
<213> ORGANISM: Hepatitis B virus

<400> SEQUENCE: 115
tcaaacactg tttcagaaaa cttcctgtta acaggcctat tgattggaaa gtatgtcaaa    60
gaattgtggg tcttttgggc tttgctgctc catttacaca atgtg                   105

<210> SEQ ID NO 116
<211> LENGTH: 105
<212> TYPE: DNA
<213> ORGANISM: Hepatitis B virus

<400> SEQUENCE: 116
tcaaacactg ttttagaaaa cttcctgtca atcgacctat tgattggaaa gtatgtcaga    60
gaattgtggg tcttttgggc tttgccgctc catttacaca atgtg                   105

<210> SEQ ID NO 117
<211> LENGTH: 105
<212> TYPE: DNA
<213> ORGANISM: Hepatitis B virus

<400> SEQUENCE: 117
tcaaactatg ttttaggaaa cttcctgtaa acaggcctat tgattggaaa gtatgtcaac    60
gaattgtggg tcttctgggg ttcgctgccc cttttacaca atgtg                   105

<210> SEQ ID NO 118
<211> LENGTH: 105
<212> TYPE: DNA
<213> ORGANISM: Hepatitis B virus

<400> SEQUENCE: 118
tcaaacaatg ttttaggaaa cttcctgtaa acaggcctat tgattggaaa gtatgtcaac    60
gaattgtggg tcttttggga tttgctgctc cttcacaca atgtg                    105

<210> SEQ ID NO 119
<211> LENGTH: 105
<212> TYPE: DNA
<213> ORGANISM: Hepatitis B virus

<400> SEQUENCE: 119
tcaaagactg ttttagaaaa ctccctgtta accggcctat tgattggaaa gtatgtcaaa    60
gaattgtggg tctcttgggc tttgctgccc cttttacaca atgtg                   105

<210> SEQ ID NO 120
```

```
<211> LENGTH: 105
<212> TYPE: DNA
<213> ORGANISM: Hepatitis B virus

<400> SEQUENCE: 120
tcaaagactg ttttagaaaa ctccctgtta atcggcctat tgattggaaa gtatgtcaaa      60
gaattgtggg tctgttgggc tttgctgccc cttttacaca atgtg                    105

<210> SEQ ID NO 121
<211> LENGTH: 105
<212> TYPE: DNA
<213> ORGANISM: Hepatitis B virus

<400> SEQUENCE: 121
tcaagcaatg ttttcgaaaa ctgcctgtaa atagacctat tgattggaaa gtatgtcaga      60
gaattgtggg tcttttgggc tttgctgccc cttttacaca atgtg                    105

<210> SEQ ID NO 122
<211> LENGTH: 105
<212> TYPE: DNA
<213> ORGANISM: Hepatitis B virus

<400> SEQUENCE: 122
ttaagaactg ttttcgaaaa ctgcctgtaa atagacctat tgattggaaa gtatgtcaaa      60
gaattgtggg tcttttgggc tttgctgccc cttttacaca atgtg                    105

<210> SEQ ID NO 123
<211> LENGTH: 105
<212> TYPE: DNA
<213> ORGANISM: Hepatitis B virus

<400> SEQUENCE: 123
tcaagcaatg ttttcgaaaa ttgcctgtaa atagacctat tgattggaaa gtatgtcaaa      60
gaattgtggg tcttttaggc tttgctgccc catttacaca atgtg                    105

<210> SEQ ID NO 124
<211> LENGTH: 105
<212> TYPE: DNA
<213> ORGANISM: Hepatitis B virus

<400> SEQUENCE: 124
tcaaacaatg ttttcggaaa ctgcctgtta atagacctat tgattggaaa gtatgtcaac      60
gaattgtggg tcttttgggc tttgctgccc cttttacaca atgtg                    105

<210> SEQ ID NO 125
<211> LENGTH: 105
<212> TYPE: DNA
<213> ORGANISM: Hepatitis B virus

<400> SEQUENCE: 125
tcaaacaatg ttttcggaaa cttcctataa atagacctat tgattggaaa gtatgtcaac      60
gaattgtggg gcttctgggc tttgccgctc cctttacaca atgtg                    105

<210> SEQ ID NO 126
<211> LENGTH: 105
<212> TYPE: DNA
<213> ORGANISM: Hepatitis B virus

<400> SEQUENCE: 126
tcaagcaatg ttttcggaaa cttcctgtaa atagacctat tgattggaaa gtatgtcaac      60
```
gaattgtggg gcttctgggc tttgccgctc cctttacaca atgtg    105

<210> SEQ ID NO 127
<211> LENGTH: 105
<212> TYPE: DNA
<213> ORGANISM: Hepatitis B virus

<400> SEQUENCE: 127
tcaaacaatg ttttcggaaa cttcctataa atagacctat tgattggaaa gtatgtcaac    60
gaattgtggg gcttctgggc tttgccgctc cctttacaca atgtg    105

<210> SEQ ID NO 128
<211> LENGTH: 105
<212> TYPE: DNA
<213> ORGANISM: Hepatitis B virus

<400> SEQUENCE: 128
tcaaacaatg ttttcggaaa cttcctataa atagacctat tgattggaaa gtatgtcaac    60
gaattgtggg gcttctgggc tttgccgctc cctttacaca atgtg    105

<210> SEQ ID NO 129
<211> LENGTH: 105
<212> TYPE: DNA
<213> ORGANISM: Hepatitis B virus

<400> SEQUENCE: 129
tgaaacaatg ttttcggaaa cttcctataa atagacctat tgattggaaa gtatgtcaaa    60
gaattgtggg tcttctgggc tttgccgccc cttttacaca atgtg    105

<210> SEQ ID NO 130
<211> LENGTH: 105
<212> TYPE: DNA
<213> ORGANISM: Hepatitis B virus

<400> SEQUENCE: 130
tcaaagattg ttttcggaaa cttcctgtaa atcgtccaat tgattggaaa gtttgtcagc    60
gcattgtggg tcttttgggc tttgcggccc ctttcaccca atgtg    105

<210> SEQ ID NO 131
<211> LENGTH: 105
<212> TYPE: DNA
<213> ORGANISM: Hepatitis B virus

<400> SEQUENCE: 131
tcaaagattg ttttcggaaa cttcctgtaa atcgtccaat tgattggaaa gtttgtcagc    60
gcattgtggg tcttttgggc tttgcggccc ctttcaccca atgtg    105

<210> SEQ ID NO 132
<211> LENGTH: 105
<212> TYPE: DNA
<213> ORGANISM: Hepatitis B virus

<400> SEQUENCE: 132
tcaaagattg ttttcgtaaa cttcctgtaa atcgccctat tgattggaaa gtttgtcaac    60
gcattgtggg tcttttgggc tttgccgccc cctttactca atgtg    105

<210> SEQ ID NO 133
<211> LENGTH: 105
<212> TYPE: DNA
<213> ORGANISM: Hepatitis B virus -continued

<400> SEQUENCE: 133
tcaaagattg ctttcgcaaa cttcccgtga atagacccat tgattggaag gtttgtcaac    60
gcattgtggg tcttttgggc tttgcagccc cttttactca atgtg                   105

<210> SEQ ID NO 134
<211> LENGTH: 25
<212> TYPE: DNA
<213> ORGANISM: Artificial
<220> FEATURE:
<223> OTHER INFORMATION: 1004R primer

<400> SEQUENCE: 134
ggaaagtatg tcaahgaatt gtggg                                          25

<210> SEQ ID NO 135
<211> LENGTH: 119
<212> TYPE: DNA
<213> ORGANISM: Hepatitis B virus

<400> SEQUENCE: 135
gcggactccc cgtctgtgcc ttctcatctg ccggtccgtg tgcacttcgc tttacctctg    60
cacgtcgcat ggagaccacc gtgaacgccc accaattctt gcccaaggtc ttacataag   119

<210> SEQ ID NO 136
<211> LENGTH: 119
<212> TYPE: DNA
<213> ORGANISM: Hepatitis B virus

<400> SEQUENCE: 136
gcggactccc cgtctgtgcc ttctcatctg ccggaccgtg tgcacttcgc ttcacctctg    60
cacgtcgcat ggagaccacc gtgaacgccc accacttctt gcccaaggtc ttacataag   119

<210> SEQ ID NO 137
<211> LENGTH: 119
<212> TYPE: DNA
<213> ORGANISM: Hepatitis B virus

<400> SEQUENCE: 137
gcggactccc cgtctgtgcc ttctcatctg ccggaccgtg tgcacttcgc ttcacctctg    60
cacgtcgcat ggagaccacc gtgaacgccc accaattctt gcccaaggtc ttacataag   119

<210> SEQ ID NO 138
<211> LENGTH: 119
<212> TYPE: DNA
<213> ORGANISM: Hepatitis B virus

<400> SEQUENCE: 138
gcggactccc cgtctgtgcc ttctcatctg ccggaccgtg tgcacttcgc ttcacctctg    60
cacgtcgcat ggagaccacc gtgaacgccc accgattctt gcccaaggtc ttacataag   119

<210> SEQ ID NO 139
<211> LENGTH: 119
<212> TYPE: DNA
<213> ORGANISM: Hepatitis B virus

<400> SEQUENCE: 139
gcggactccc cgtctgtgcc ttctcatctg ccggaccgtg tgcacttcgc ttcacctctg    60
cacgtcgcat ggagaccacc gtgaacgccc acaggaacct gcccaaggtc ttgcataag   119

<210> SEQ ID NO 140

```
<211> LENGTH: 119
<212> TYPE: DNA
<213> ORGANISM: Hepatitis B virus

<400> SEQUENCE: 140
gcggactccc cgtctgtgcc ttctcatctg ccggaccgtg tgcacttcgc ttcacctctg    60
cacgtcgcat ggagaccacc gtgaacgccc acaggaacct gcccaaggcc ttgcataag   119

<210> SEQ ID NO 141
<211> LENGTH: 119
<212> TYPE: DNA
<213> ORGANISM: Hepatitis B virus

<400> SEQUENCE: 141
gcggactccc cgtctgtgcc ttctcatctg ccggaccgtg tgcacttcgc ttcacctctg    60
cacgtcgcat ggagaccacc gtgaacgccc acgggaacct gcccaaggtc ttgcataag   119

<210> SEQ ID NO 142
<211> LENGTH: 119
<212> TYPE: DNA
<213> ORGANISM: Hepatitis B virus

<400> SEQUENCE: 142
gcggactccc cgtctgtgcc ttctcatctg ccggaccgtg tgcacttcgc ttcacctctg    60
cacgtcgcat ggagaccacc gtgaacgccc acgggaacct gcccaaggtc ttgcataag   119

<210> SEQ ID NO 143
<211> LENGTH: 119
<212> TYPE: DNA
<213> ORGANISM: Hepatitis B virus

<400> SEQUENCE: 143
gcggactccc cgtctgtgcc ttctcatctg ccggaccgtg tgcacttcgc ttcacctctg    60
cacgtcgcat ggagaccacc gtgaacgccc acgggaacct gcccaaggtc ttgcataag   119

<210> SEQ ID NO 144
<211> LENGTH: 119
<212> TYPE: DNA
<213> ORGANISM: Hepatitis B virus

<400> SEQUENCE: 144
gcggactccc cgtctgtgcc ttctcatctg ccggaccgtg tgcacttcgc ttcacctctg    60
cacgtcgcat ggagaccacc gtgaacgccc accggaacct gcccaaggtc ttgcataag   119

<210> SEQ ID NO 145
<211> LENGTH: 119
<212> TYPE: DNA
<213> ORGANISM: Hepatitis B virus

<400> SEQUENCE: 145
gcggactccc cgtctgtgcc ttctcatctg ccggaccgtg tgcacttcgc ttcacctctg    60
cacgtcgcat ggaaaccacc gtgaacgccc acaggaacct gcccaaggtc ttgcataag   119

<210> SEQ ID NO 146
<211> LENGTH: 119
<212> TYPE: DNA
<213> ORGANISM: Hepatitis B virus

<400> SEQUENCE: 146
gcggactccc cgtctgtgcc ttctcatcta ccggaccgtg tgcacttcgc ttcacctctg    60
```

-continued

```
cacgtcgcat ggaaaccacc gtgaacgccc actggaacct gcccaaggtc ttgcataag      119

<210> SEQ ID NO 147
<211> LENGTH: 119
<212> TYPE: DNA
<213> ORGANISM: Hepatitis B virus

<400> SEQUENCE: 147
gcggtctccc cgtctgtgcc ttctcatctg ccggtccgtg tgcacttcgc ttcacctctg      60
cacgttgcat ggagaccacc gtgaacgccc atcagatcct gcccaaggtc ttacataag      119

<210> SEQ ID NO 148
<211> LENGTH: 119
<212> TYPE: DNA
<213> ORGANISM: Hepatitis B virus

<400> SEQUENCE: 148
gcggtctccc cgtctgtgcc ttctcatctg ccggtccgtg tgcacttcgc ttcacctctg      60
cacgttgcat ggcgaccacc gtgaacgccc atcagatcct gcccaaggtc ttacataag      119

<210> SEQ ID NO 149
<211> LENGTH: 119
<212> TYPE: DNA
<213> ORGANISM: Hepatitis B virus

<400> SEQUENCE: 149
gcggtctccc cgtctgtgcc ttctcatctg ccggtccgtg tgcacttcgc ttcacctctg      60
cacgttgcat ggagaccacc gtgaacgccc atcaggtcct gcccaaggtc ttacataag      119

<210> SEQ ID NO 150
<211> LENGTH: 119
<212> TYPE: DNA
<213> ORGANISM: Hepatitis B virus

<400> SEQUENCE: 150
gcggactccc cgtctgtctc ttctctgctg ccggaccgtg tgcacttcgc ttcacctctg      60
cacgtcgcat ggagaccacc gtgaacgccc accggaacct gcccaaggtc ttacataag      119

<210> SEQ ID NO 151
<211> LENGTH: 119
<212> TYPE: DNA
<213> ORGANISM: Hepatitis B virus

<400> SEQUENCE: 151
gcggactccc cgtctgtgcc ttctcatctg ccggaccgtg tgcacttcgc ttcacctctg      60
cacgtcgcat ggagaccacc gtgaacgccc atcggaacct gcccaaggtc ttgcataag      119

<210> SEQ ID NO 152
<211> LENGTH: 119
<212> TYPE: DNA
<213> ORGANISM: Hepatitis B virus

<400> SEQUENCE: 152
gcggtctccc cgtctgtgcc ttctcgtctg ccggaccgtg tgcacttcgc ttcacctctg      60
cacgtcgcat ggagaccacc gtgaacgccc accaaatctt gcccagggtc ttacataag      119

<210> SEQ ID NO 153
<211> LENGTH: 119
<212> TYPE: DNA
<213> ORGANISM: Hepatitis B virus
```

<400> SEQUENCE: 153
gcggtctccc cgtctgtgcc ttctcatctg ccggaccgtg tgcacttcgc ttcacctctg      60
cacgtcgcat ggagaccacc gtgaacgccc accaaatctt gcccaaggtc ttacataag     119

<210> SEQ ID NO 154
<211> LENGTH: 119
<212> TYPE: DNA
<213> ORGANISM: Hepatitis B virus

<400> SEQUENCE: 154
gcggtctccc cgtctgtgcc ttctcatctg ccggtccgtg tgcacttcgc ttcacctctg      60
cacgtcgcat ggagaccacc gtgaacgccc accaggtctt gcccaaggtc ttacataag     119

<210> SEQ ID NO 155
<211> LENGTH: 119
<212> TYPE: DNA
<213> ORGANISM: Hepatitis B virus

<400> SEQUENCE: 155
gcggtctccc cgtctgtgcc ttctcatctg ccggaccgtg tgcacttcgc ttcacctctg      60
cacgtcgcat ggagaccacc gtgaacgccc accaggtctt gcccaaggtc ttgcataag     119

<210> SEQ ID NO 156
<211> LENGTH: 119
<212> TYPE: DNA
<213> ORGANISM: Hepatitis B virus

<400> SEQUENCE: 156
gcggtctccc cgtctgtgcc ttctcatctg ccggaccgtg tgcacttcgc ttcacctctg      60
cacgtcgcat ggaaaccacc gtgaacgccc accaggtctt gcccaaggtc ttatataag     119

<210> SEQ ID NO 157
<211> LENGTH: 119
<212> TYPE: DNA
<213> ORGANISM: Hepatitis B virus

<400> SEQUENCE: 157
gcggtctccc cgtctgtgcc ttctcatctg ccggtccgtg tgcacttcgc ttcacctctg      60
cacgtcgcat ggagaccacc gtgaacgccc accaggtctt gcccaaggtc ttacataag     119

<210> SEQ ID NO 158
<211> LENGTH: 119
<212> TYPE: DNA
<213> ORGANISM: Hepatitis B virus

<400> SEQUENCE: 158
gcggtctccc cgtctgtgcc ttctcatctg ccggaccgtg tgcacttcgc ttcacctctg      60
cacgtcgcat ggagaccacc gtgaacaccc gacaggtctt gcccaaggtc ttacataag     119

<210> SEQ ID NO 159
<211> LENGTH: 119
<212> TYPE: DNA
<213> ORGANISM: Hepatitis B virus

<400> SEQUENCE: 159
gcggtctccc cgtctgtgcc ttctcatctg ccggaccgtg tgcacttcgc ttcacctctg      60
tacgtcgcat ggaaaccacc gtgaacgccc aataggtctt gcccaaggtc ttacataag     119

<210> SEQ ID NO 160

```
<211> LENGTH: 119
<212> TYPE: DNA
<213> ORGANISM: Hepatitis B virus

<400> SEQUENCE: 160
gcggtctccc cgtctgtgcc ttctcatctg ccggaccgtg tgcacttcgc ttcacctctg      60
cacgtcgcat ggagaccacc gtgaacgccc gacaggcctt gcccaaggtc ttacataag     119

<210> SEQ ID NO 161
<211> LENGTH: 119
<212> TYPE: DNA
<213> ORGANISM: Hepatitis B virus

<400> SEQUENCE: 161
gcggtctccc cgtctgtgcc ttctcatctg ccggaccgtg tgcacttcgc ttcacctctg      60
cacgtcgcat ggagaccacc gtgaacgccc gacaggtctt gcccaaggtc ttacataag     119

<210> SEQ ID NO 162
<211> LENGTH: 119
<212> TYPE: DNA
<213> ORGANISM: Hepatitis B virus

<400> SEQUENCE: 162
gcggtctccc cgtctgtgcc ttctcatctg ccggaccgtg tgcacttcgc ttcacctctg      60
cacgtcgcat ggagaccacc gtgaacgcct gccaggtctt gcccaaggtc ttacataag     119

<210> SEQ ID NO 163
<211> LENGTH: 119
<212> TYPE: DNA
<213> ORGANISM: Hepatitis B virus

<400> SEQUENCE: 163
gcggactccc cgtctgttcc ttctcatctg ccggaccgtg tgcacttcgc ttcacctctg      60
cacgtcgcat ggagaccacc gtgaacgccc cctggaatct gccaacagtc ttacataag     119

<210> SEQ ID NO 164
<211> LENGTH: 119
<212> TYPE: DNA
<213> ORGANISM: Hepatitis B virus

<400> SEQUENCE: 164
gcggactccc cgtctgttcc ttctcatctg ccggaccgtg tgcacttcgc ttcacctctg      60
cacgtcgcat ggagaccacc gtgaacgccc cctggaatct gccaacagtc ttacataag     119

<210> SEQ ID NO 165
<211> LENGTH: 119
<212> TYPE: DNA
<213> ORGANISM: Hepatitis B virus

<400> SEQUENCE: 165
gcggcctccc cgtctgttcc ttctcatctg ccggaccgtg tgcacttcgc ttcacctctg      60
cacgtcgcat ggagaccacc gtgaacgccc ctcgaagctt gccaacagtc ttacataag     119

<210> SEQ ID NO 166
<211> LENGTH: 119
<212> TYPE: DNA
<213> ORGANISM: Hepatitis B virus

<400> SEQUENCE: 166
gcggactccc cgcctgtgcc ttctcatctg ccggaccgtg tgcacttcgc ttcacctctg      60
```

```
cacgtcacat ggagaccacc gtgaacgccc ctcggaactt gccaacaacc ttatataag    119
```

```
<210> SEQ ID NO 167
<211> LENGTH: 20
<212> TYPE: DNA
<213> ORGANISM: Artificial
<220> FEATURE:
<223> OTHER INFORMATION: 1593F primer

<400> SEQUENCE: 167
acctctgcac gtyrcatgga                                                20
```

```
<210> SEQ ID NO 168
<211> LENGTH: 130
<212> TYPE: DNA
<213> ORGANISM: Hepatitis B virus

<400> SEQUENCE: 168
ctactgttca agcctccaag ctgtgccttg ggtggctttg gggcatggac attgacccttt   60 ataaagaatt tggagctact gtggagttac tctcgttttt gccttctgac ttctttcctt   120
cagtacgaga                                                           130
```

```
<210> SEQ ID NO 169
<211> LENGTH: 130
<212> TYPE: DNA
<213> ORGANISM: Hepatitis B virus

<400> SEQUENCE: 169
ctactgttca agcctccaag ctgtgccttg ggtggctttg gggcatggac attgacccttt   60 ataaagaatt tggagctact gtggagttac tctcgttttt gccttctgac ttctttcctt   120
cagtacgaga                                                           130
```

```
<210> SEQ ID NO 170
<211> LENGTH: 130
<212> TYPE: DNA
<213> ORGANISM: Hepatitis B virus

<400> SEQUENCE: 170
ctactgttca agcctccaag ctgtgccttg ggtggctttg ggacatggac attgacccttt   60 ataaagaatt tggagctact gtggagttac tctcttttttt gccttctgac ttctttcctt  120
cttttcgaga                                                           130
```

```
<210> SEQ ID NO 171
<211> LENGTH: 130
<212> TYPE: DNA
<213> ORGANISM: Hepatitis B virus

<400> SEQUENCE: 171
ctactgttca agcctccaag ctgtgccttg ggtggctttg gggcatggac attgatccttt   60 ataaagaatt tggagctact gtggagttac tctcgttttt gccttctgac ttctttcctt   120
cagtacgaga                                                           130
```

```
<210> SEQ ID NO 172
<211> LENGTH: 130
<212> TYPE: DNA
<213> ORGANISM: Hepatitis B virus

<400> SEQUENCE: 172
ctactgttca agcctccaag ctgtgccttg ggtggctttg gggcatggac attgaccgt    60
```

```
ataaagaatt tggagcttct gtggagttac tctcttttttt gccttctgac ttctttcctt    120
ctattcgaga                                                            130

<210> SEQ ID NO 173
<211> LENGTH: 130
<212> TYPE: DNA
<213> ORGANISM: Hepatitis B virus

<400> SEQUENCE: 173
ctactgttca agcctccaag ctgtgccttg ggtggctttg gggcatggac attgacccgt     60
ataaagaatt tggagcttct gtggagttac tctcttttttt gcctactgac ttctttcctt   120
ctattcgaga                                                            130

<210> SEQ ID NO 174
<211> LENGTH: 130
<212> TYPE: DNA
<213> ORGANISM: Hepatitis B virus

<400> SEQUENCE: 174
ctactgttca agcctccaag ctgtgccttg ggtggctttg gggcatggac attgacccgt     60
ataaagaatt tggagcttct gtggagttac tctcttttttt gcctgctgac ttctttcctt   120
ctattcgaga                                                            130

<210> SEQ ID NO 175
<211> LENGTH: 130
<212> TYPE: DNA
<213> ORGANISM: Hepatitis B virus

<400> SEQUENCE: 175
ctactgttca agcctccaag ctgtgccttg ggtggctttg gggcatggac attgacccgt     60
ataaagaatt tggagcttct gtggagttac tctcttttttt gccttctgac ttctttcctt   120
ctattcgaga                                                            130

<210> SEQ ID NO 176
<211> LENGTH: 129
<212> TYPE: DNA
<213> ORGANISM: Hepatitis B virus

<400> SEQUENCE: 176
ctactgttca agcctccaag ctgtgccttg ggtggctttg gggcatggac attgacccgt     60
ataaagaatt tggagcttct gtggagttac tctctttttg ccttctgact tctttccttc    120
tattcgaga                                                            129

<210> SEQ ID NO 177
<211> LENGTH: 130
<212> TYPE: DNA
<213> ORGANISM: Hepatitis B virus

<400> SEQUENCE: 177
ctactgttca agcctccaag ctgtgccttg ggtggctttg gggcatggac attgacccgt     60
ataaagaatt tggagcttct gtggagttac tctcttttttt gccttctgac ttctttcctt   120
ctattcgaga                                                            130

<210> SEQ ID NO 178
<211> LENGTH: 130
<212> TYPE: DNA
<213> ORGANISM: Hepatitis B virus
```

-continued

```
<400> SEQUENCE: 178
ctactgttca agcctccaag ctgtgccttg ggtggcttta ggacatggac attgacacgt      60
ataaagaatt tggagcttct gtggagttac tctcttttt gccttctgac ttctttcctt     120
ctgttcgaga                                                            130

<210> SEQ ID NO 179
<211> LENGTH: 130
<212> TYPE: DNA
<213> ORGANISM: Hepatitis B virus

<400> SEQUENCE: 179
ctactgttca agcctccaag ctgtgccttg ggtggcttta gggcatggac attgacacgt      60
ataaagaatt tggagcttct gtggagttac tctcttttt gccttctgac ttctttcctt     120
ctattcgaga                                                            130

<210> SEQ ID NO 180
<211> LENGTH: 130
<212> TYPE: DNA
<213> ORGANISM: Hepatitis B virus

<400> SEQUENCE: 180
ccactgttca agcctccaag ctgtgccttg ggtggctttg gggcatggac attgacccctt     60 ataaagaatt tggagctact gtggagttac tctcgttttt gccttctgac ttctttcctt    120
ccgtcagaga                                                            130

<210> SEQ ID NO 181
<211> LENGTH: 130
<212> TYPE: DNA
<213> ORGANISM: Hepatitis B virus

<400> SEQUENCE: 181
ccactgttca agcctccaag ctgtgccttg ggtggctttg gggcatggac attgacccctt     60 ataaagaatt tggagctact gtggagttac tctcgttttt gccttctgac ttctttcctt    120
ccgtcagaga                                                            130

<210> SEQ ID NO 182
<211> LENGTH: 130
<212> TYPE: DNA
<213> ORGANISM: Hepatitis B virus

<400> SEQUENCE: 182
ccacttttca agcctccaag ctgtgccttg gatggctttg gggcatggac attgacccctt     60 ataaagaatt tggagctact gtggagttac tctcattttt gccttctgac ttctttcctt    120
ccgtccggga                                                            130

<210> SEQ ID NO 183
<211> LENGTH: 130
<212> TYPE: DNA
<213> ORGANISM: Hepatitis B virus

<400> SEQUENCE: 183
ctactgttca agcctccaag ctgtgtcttg ggtggctttg ggccatggac attgacccgt      60
ataaagaatt tggagcttct gtggagttac tctcttttt gccctctgac ttttttcctt     120
ctattcgaga                                                            130

<210> SEQ ID NO 184
```

```
<211> LENGTH: 130
<212> TYPE: DNA
<213> ORGANISM: Hepatitis B virus

<400> SEQUENCE: 184
ctactgttca agcctccaag ctgtgccttg ggtggctttg gggcatggac attgacacct      60
ataaagaatt tggagcttct gtggagttac tctcttttt gccttctgac ttctttcctt     120
ctattcgaga                                                            130

<210> SEQ ID NO 185
<211> LENGTH: 130
<212> TYPE: DNA
<213> ORGANISM: Hepatitis B virus

<400> SEQUENCE: 185
ctactgttca agcctccaag ctgtgccttg ggtggctttg gggcatggac attgacccett     60 ataaagaatt tggagctact gtggagttac tctcgtttt gccttctgac ttctttcctt     120
cagtaagaga                                                            130

<210> SEQ ID NO 186
<211> LENGTH: 130
<212> TYPE: DNA
<213> ORGANISM: Hepatitis B virus

<400> SEQUENCE: 186
ctactgttca agcctccaag ctgtgccttg ggtggcttta ggacatggac attgacccett     60 ataaagaatt tggagcttct gtggagttac tctcgtttt gcctactgac ttctttcctt     120
ccgtaagaga                                                            130

<210> SEQ ID NO 187
<211> LENGTH: 130
<212> TYPE: DNA
<213> ORGANISM: Hepatitis B virus

<400> SEQUENCE: 187
ctactgttca agcctccaag ctgtgccttg ggtggctttg gggcatggac attgacccgt      60
ataaagaatt tggagcttct gtggagttac tctcttttt gccttctgac ttctttcctt     120
ctattcgaga                                                            130

<210> SEQ ID NO 188
<211> LENGTH: 130
<212> TYPE: DNA
<213> ORGANISM: Hepatitis B virus

<400> SEQUENCE: 188
ctactgttca agcctccaag ctgtgccttg ggtggcttta ggacatggac atcgacccat      60
ataaagaatt tggagcctct gctgagttac tctcttttt gccttctgac ttctttccgt     120
ctattcgaga                                                            130

<210> SEQ ID NO 189
<211> LENGTH: 130
<212> TYPE: DNA
<213> ORGANISM: Hepatitis B virus

<400> SEQUENCE: 189
ctactgttca agcctccaag ctgtgccttg ggtggctttg gggcatggac attgacacct      60
ataaagaatt tggagcttct gtggagttac tctcgtttat gccttctgac ttctttcctt     120
```

```
ctattcgaga                                                            130

<210> SEQ ID NO 190
<211> LENGTH: 130
<212> TYPE: DNA
<213> ORGANISM: Hepatitis B virus

<400> SEQUENCE: 190
ctactgttca agcctccaag ctgtgccttg ggtggctttg gggcatggac attgacccgt     60
ataaagaatt tggagcttct gtggagttac tctcttttt gccttctgac ttctttcctt    120
ccattcgaga                                                            130

<210> SEQ ID NO 191
<211> LENGTH: 130
<212> TYPE: DNA
<213> ORGANISM: Hepatitis B virus

<400> SEQUENCE: 191
ccactgttca agcctccaag ctgtgccttg ggtggctttg gggcatggac attgacccgt     60
ataaagaatt tggagcttct gtggagttac tctcttttt gccttctgac ttctttcctt    120
ctattcgtga                                                            130

<210> SEQ ID NO 192
<211> LENGTH: 130
<212> TYPE: DNA
<213> ORGANISM: Hepatitis B virus

<400> SEQUENCE: 192
ctactgttca agcctccaag ctgtgccttg ggtggctttg gggcatggac attgacccgt     60
ataaagaatt tggagcttct gtggagttac tctcttttt gccttctgac ttctttcctt    120
ctattcgtga                                                            130

<210> SEQ ID NO 193
<211> LENGTH: 130
<212> TYPE: DNA
<213> ORGANISM: Hepatitis B virus

<400> SEQUENCE: 193
ccactgttca agcctccaag ctgtgccttg ggtggctttg gggcatggac attgacccgt     60
ataaagaatt cggagcttct gtggagttac tctcttttt gccttctgac ttctttcctt    120
ctgttcgtga                                                            130

<210> SEQ ID NO 194
<211> LENGTH: 130
<212> TYPE: DNA
<213> ORGANISM: Hepatitis B virus

<400> SEQUENCE: 194
ccactgttca agcctccaag ctgtgccttg ggtggctttg gggcatggac attgacccgt     60
ataaagaatt tggagcttct gtggagttac tctcttttt gccttctgac ttctttcctt    120
ctattcgtga                                                            130

<210> SEQ ID NO 195
<211> LENGTH: 130
<212> TYPE: DNA
<213> ORGANISM: Hepatitis B virus

<400> SEQUENCE: 195
```

```
ctactgttca agcctccaag ctgtgccttg ggtggctttg gggcatggac attgacccga    60
ataaagaatt tggagcttct gtggagttac tctctttttt gccttctgac ttcttttcctt  120 ctattcgtga                                                          130

<210> SEQ ID NO 196
<211> LENGTH: 130
<212> TYPE: DNA
<213> ORGANISM: Hepatitis B virus

<400> SEQUENCE: 196
ccactgttca agcctccaag ctgtgccttg ggtggctttg gggcatggac attgacccTT   60
ataaagaatt tggagcttct gtggaattgc tctctttttt gccttctgat ttcttcccgt  120
ctgttcggga                                                          130

<210> SEQ ID NO 197
<211> LENGTH: 130
<212> TYPE: DNA
<213> ORGANISM: Hepatitis B virus

<400> SEQUENCE: 197
ccactgttca agcctccaag ctgtgccttg ggtggctttg gggcatggac attgacccTT   60
ataaagaatt tggcgcttct gtggaattgc tctctttttt gccttctgat ttcttcccgt  120
ctgttcggga                                                          130

<210> SEQ ID NO 198
<211> LENGTH: 130
<212> TYPE: DNA
<213> ORGANISM: Hepatitis B virus

<400> SEQUENCE: 198
ctactgttca agcctccaag ctgtgccttg ggtggcttta gggcatggac attgacccTT   60
ataaagaatt tggagcttct gtggaattac tctctttttt gcctactgat ttcttcccgt  120
cagttcggga                                                          130

<210> SEQ ID NO 199
<211> LENGTH: 130
<212> TYPE: DNA
<213> ORGANISM: Hepatitis B virus

<400> SEQUENCE: 199
ccactgttca agcctccaag ctgtgccttg ggtggctttg gggcatggac attgacccTT   60
ataaagaatt tggagcttct gcggagttac tctcattttt gccttctgac ttcttcccgt  120
ctgtccggga                                                          130

<210> SEQ ID NO 200
<211> LENGTH: 25
<212> TYPE: DNA
<213> ORGANISM: Artificial
<220> FEATURE:
<223> OTHER INFORMATION: 1950R primer

<400> SEQUENCE: 200
ttggagctac tgtggagtta ctctc                                          25
```

MULTIPLEX DETECTION OF HEPATITIS VIRUS VARIATIONS

This application claims priority from U.S. Provisional Application Ser. No. 61/175,827 filed May 6, 2009. The entirety of that provisional application is incorporated herein by reference.

FIELD

The present invention generally relates to a method and a kit for the detection of virus variations.

BACKGROUND

Hepatitis is an inflammation of the liver, most commonly caused by a viral infection. There are five main hepatitis viruses, referred to as types A, B, C, D and E.

Hepatitis A and E are typically caused by ingestion of contaminated food or water. Hepatitis B, C and D usually occur as a result of parenteral contact with infected body fluids (e.g. from blood transfusions or invasive medical procedures using contaminated equipment). Hepatitis B is also transmitted by sexual contact.

Worldwide, it is estimated that 400 million people are chronically infected with hepatitis B virus (HBV). Chronic hepatitis B (CHB) infection is the most common cause of liver cirrhosis and hepatocellular carcinoma (HCC), with an estimated 500,000-900,000 death per year. Continuing HBV replication increases the risk of progression to cirrhosis and HCC (28-31).

Variations in the hepatitis B virus (HBV) genome may develop spontaneously or under selective pressure from antiviral therapy. Some of these variations confer drug resistance, resulting in treatment failure which may further lead to hepatitis reactivation and hepatic decompensation (32).

SUMMARY

One aspect is to provide a method for the detection of hepatitis virus (HV) variations, comprising a) providing a DNA molecule of an HV from a subject suffering from the HV infection as a template, wherein the DNA molecule includes an HV variation site; b) extending multiplex extension primers along the template to obtain extension products containing nucleotides at the variation sites; and c) analyzing the extension products by mass spectrometry (MS) to detect the HV variations.

Another aspect is to provide a method for the treatment of a hepatitis virus (HV) infection in a subject, comprising a) detecting HV variations in the subject according to the detection method disclosed herein, where the HV variations are in association with drug resistance; b) assessing the drug resistance of the subject based on the detection; and c) treating the subject based on the assessment.

Yet another aspect is to provide a kit for the detection of hepatitis virus (HV) variations by mass spectrometry analysis, comprising multiplex extension primers disclosed herein.

BRIEF DESCRIPTION OF THE DRAWINGS

FIG. 3 is an extension reaction thermal profile. A 200-short-cycle program with two cycling loops was used for extension reaction. The 5-cycle loop sat inside the 40-cycle loop.

Figure 4A:
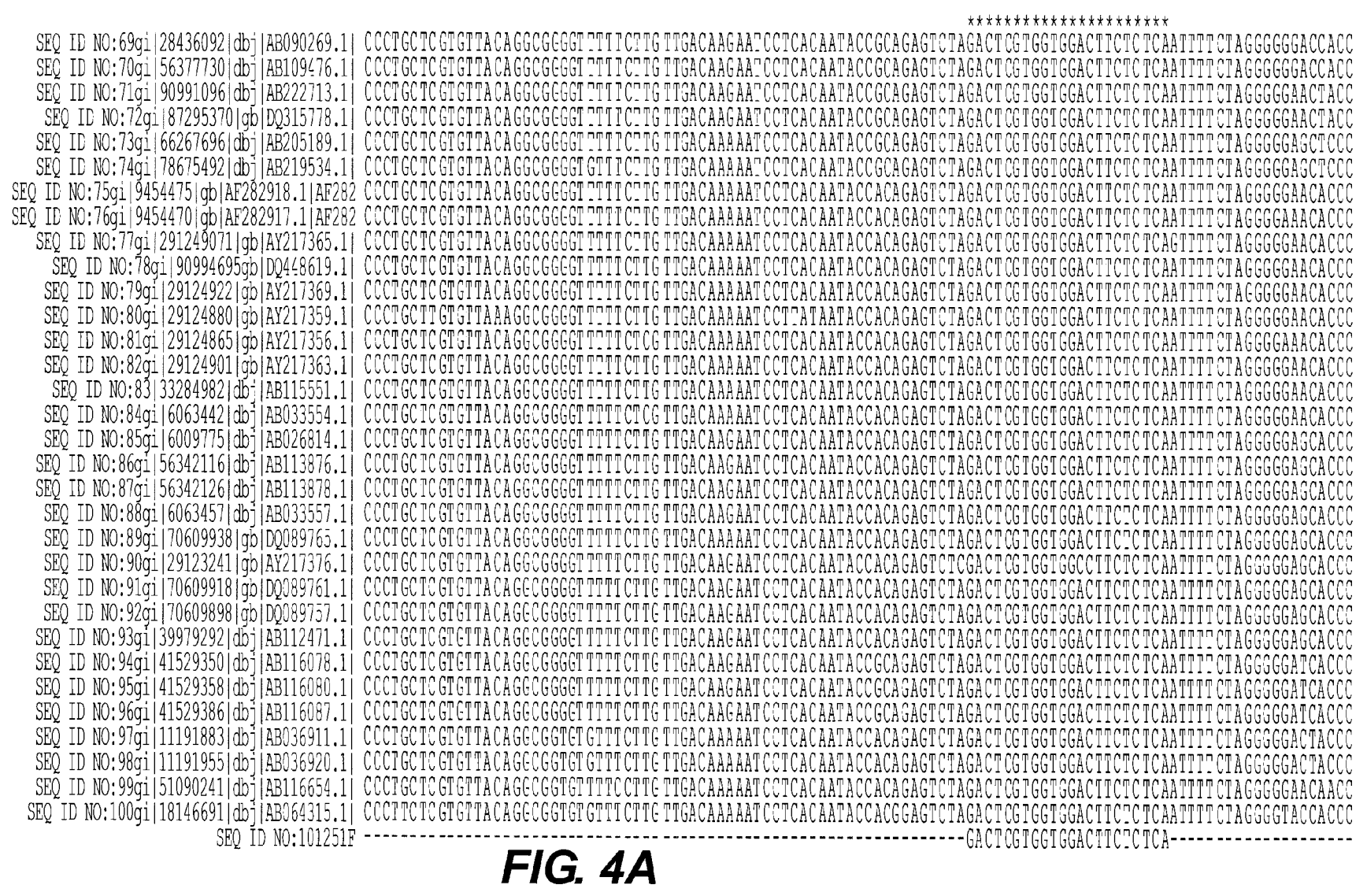
Figure 4B:
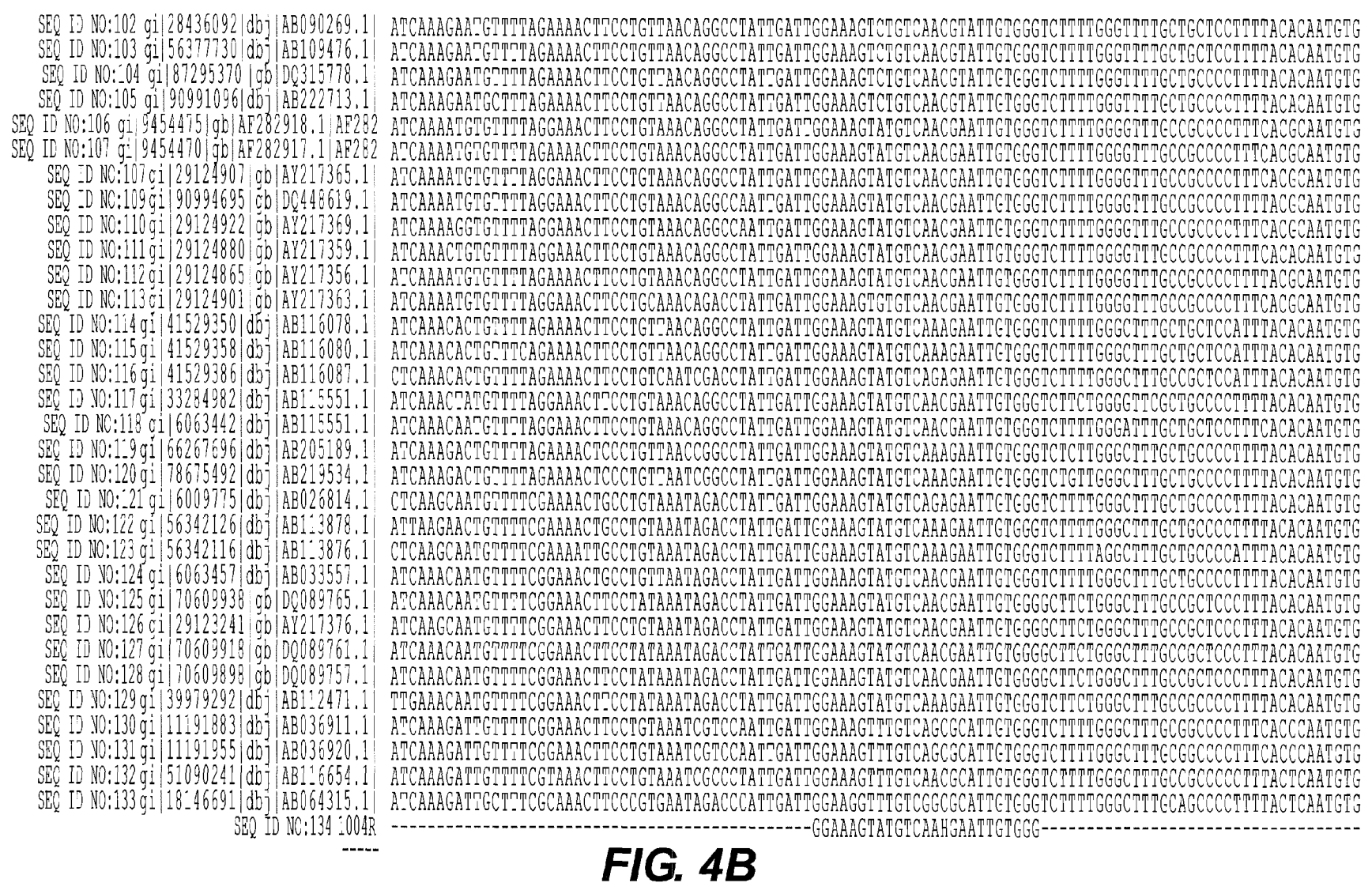
Figure 4C:
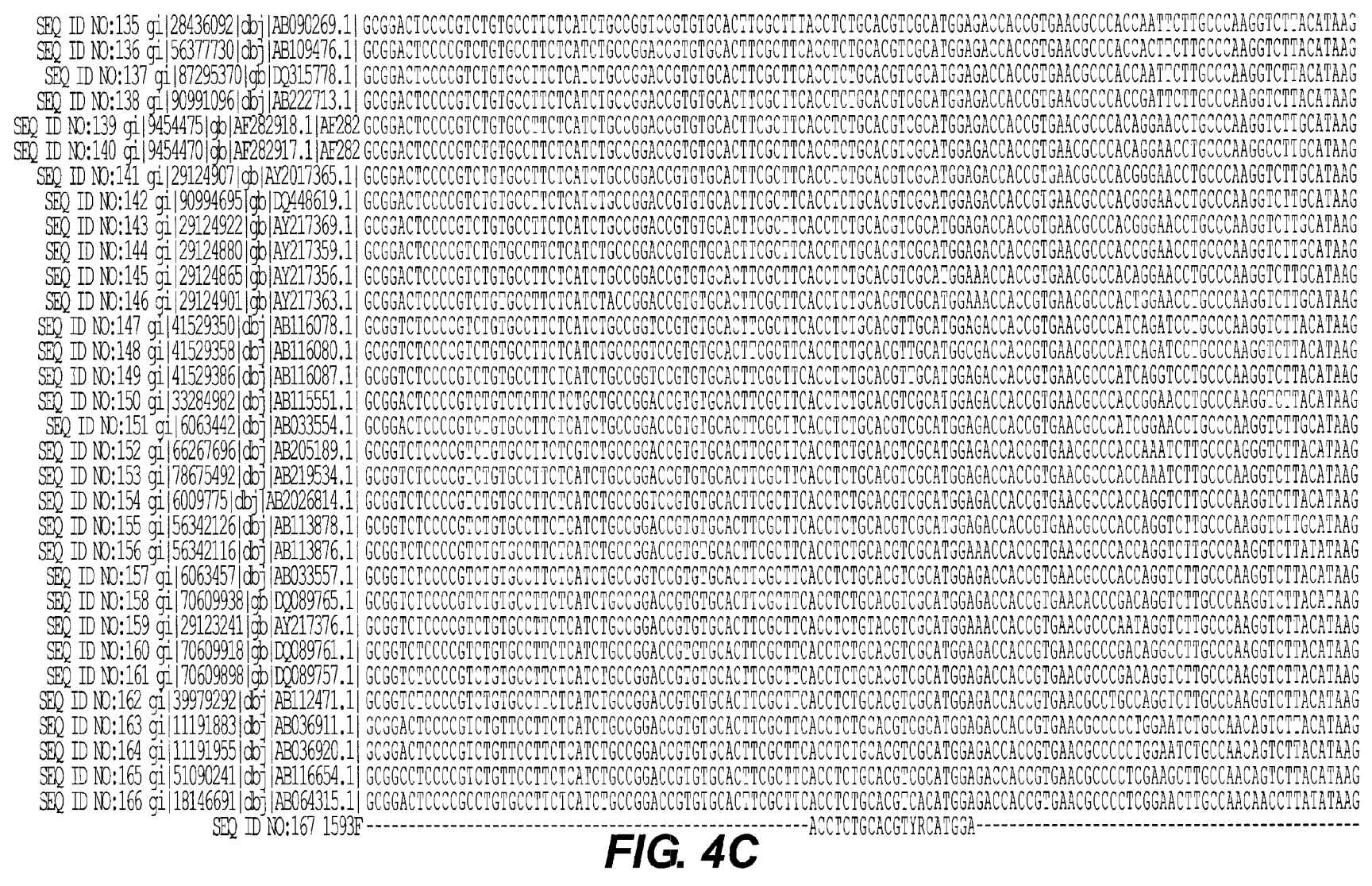
Figure 4D:
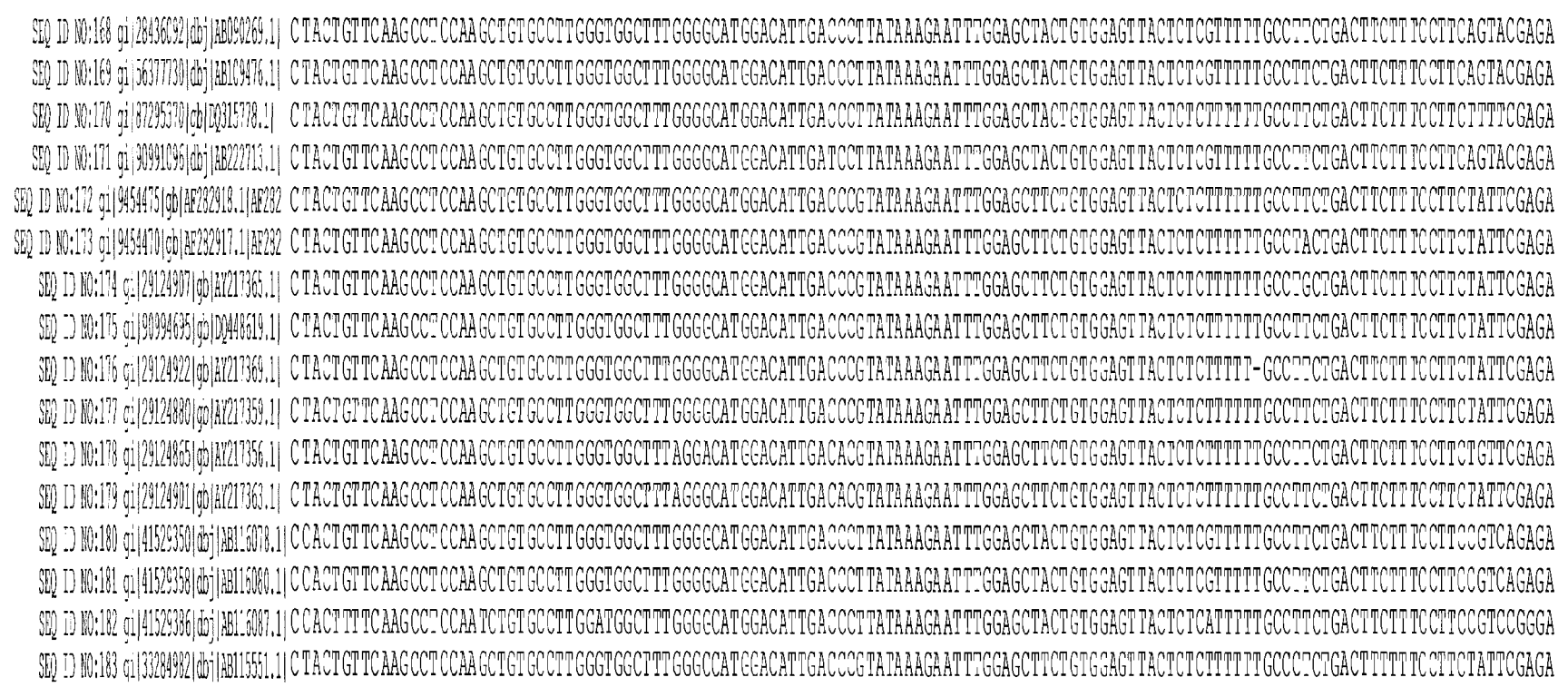
Figure 4D:
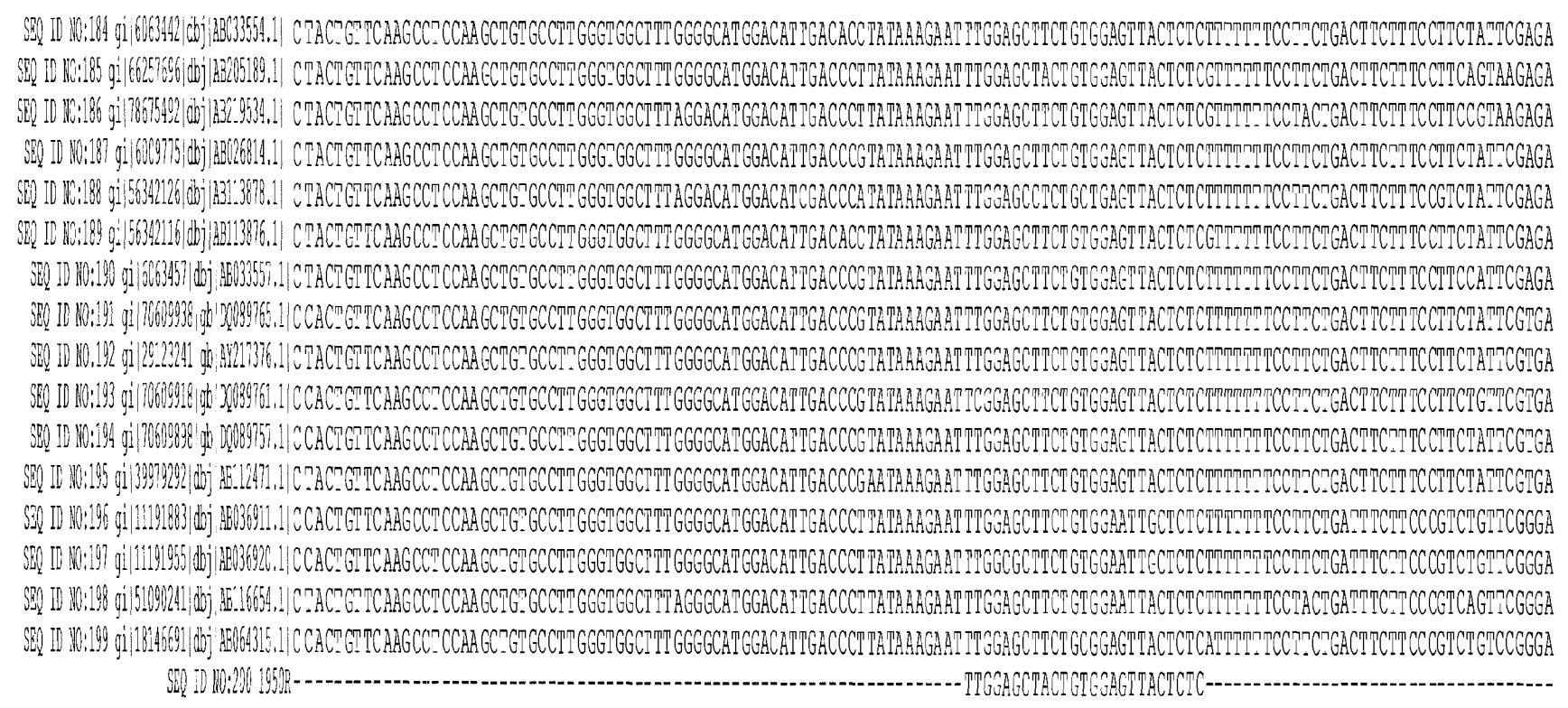

FIGS. 4A-4E depict alignment of PCR primers to different HBV genotypes. Four primers were designed, 251F and 1004R for the reverse transcriptase, and 1593F and 1950R for precore and core promoters.

FIG. 5 is an exemplified mass spectrum. Panel a) MS detected both wild type and mutant sequences while sequencing only detected one sequence; panel b) sequencing detected both wild type and mutant sequences while MS only detected one sequence.

FIG. 6 shows examples of extension primers. MW stands for molecular weight, UEP for an unextended primer, and EP for an extended primer.

DETAILED DESCRIPTION

Figure 1:
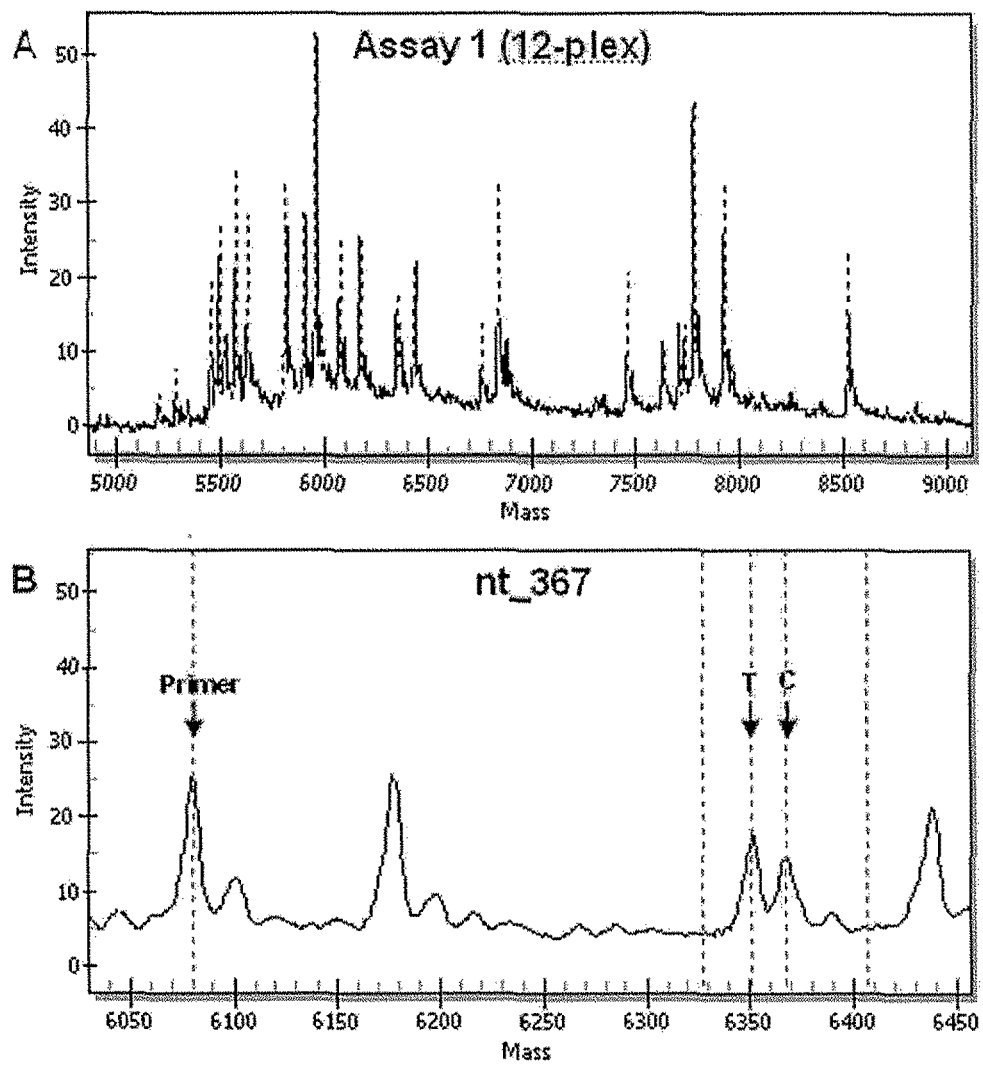
FIG. 1 is a representative mass spectrum for multiplex extension assay 1. The entire raw spectrum is shown in panel a. The intensities for the peaks are arbitrary units. Panel b zooms in one assay (nt_367). "Primer" represents the unextended primer. T and C represent the extension products for the mutant sequence (T) and wild type sequence (C), respectively.

The practice of the present invention will employ, unless otherwise indicated, conventional methods of molecular biology, virology, cell biology, microbiology and biochemistry within the skill of the art. Such techniques are explained fully in the literature. All publications, patents and patent applications cited herein, whether supra or infra, are hereby incorporated by reference in their entirety.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example to understand the document where the term is originally used).

As used herein, the term "variation" refers to the genetic variation of a virus.

As used herein, the term "variation site" is intended to mean the nucleotide site where a variation is present.

As used herein, the term "DNA" is intended to mean any polymer of deoxynucleotides.

As used herein, the term "complementary" or "complementarity" is used in reference to nucleotide/polynucleotides related by the base-pairing rules. For polynucleotides, "complementary" may be "partial," in which only some of the polynucleotides' bases are matched according to the base-pairing rules. Or, there may be "complete" or "total" complementarity between the polynucleotides.

One aspect disclosed herein is directed to a method for the detection of hepatitis virus (HV) variations, comprising the steps of a) providing a DNA molecule of an HV from a subject suffering from the HV infection as a template, wherein the DNA molecule includes an HV variation site; b) extending multiplex extension primers along the template to obtain extension products containing nucleotides at the variation sites; and c) analyzing the extension products by mass spectrometry (MS) to detect the HV variations.

Exemplary HVs are hepatitis A, B, C and D viruses. Preferably, the HV is an HBV.

HV variations occur at much higher density on an HV genome as compared with human SNPs. HV may exist as quasi-species such that some HV variations may only be present at a minor proportion, while heterozygous SNPs are present at 1:1 ratio. The HV variations include, but not limited to, variations in association with virulence, viral escape and/or drug resistance of an HV. In some embodiments, the HV variations are variations in association with drug resistance of an HV, including HV variations that have been documented for their functional roles in drug resistance and/or HV variations that have been detected in serum samples derived from patients undergoing an anti-HV therapy. In a particular embodiment, where the HV is an HBV, the variations which are associated with drug resistance are exemplarily listed in Table 1.

TABLE 1

Summary of mutations

| HBV Region | Amino acid substitutions | Nucleotide changes | Reference |
|---|---|---|---|
| Reverse transcriptase | rtT70S | A/T@337 | (1) |
| | rtN71T | A/C@341 | (1) |
| | rtS78T | T/A@361 | (2) |
| | rtL80I(V) | C/T/A/G@367 | (3) |
| | rtL82M | C/A@373 | (2, 4) |
| | rtV84M | G/A@379 | (5) |
| | rtS85A | T/G@382 | (5) |
| | rtA86P | G/C@385 | (1) |
| | rtP92L | C/T@404 | (1) |
| | rtT128N | C/A@512 | (6) |
| | rtH133L | A/T@527 | (7) |
| | rtS/T135C | A/T@532 | (4) |
| | | C/G@533 | |
| | rtI/V163V | A/G@616 | (2) |
| | rtF166L | T/C@ 625 | (8) |
| | rtI169T | T/C@635 | (9) |
| | rtV173L | G/C/T@646 | (10) |
| | rtP177L | C/T@659 | (2) |
| | rtL179P | T/C@665 | (11) |
| | rtL180M | C/T/A@667 | (12) |
| | rtA181T(V/S) | G/A/T@670 | (13) |
| | | C/T@671 | |
| | rtT184G | A/G@679 | (9) |
| | | C/G@680 | |
| | rtV191I | G/A@700 | (1) |
| | rtA194T | G/A@709 | (14) |
| | rtA200V | C/T@728 | (2) |
| | rtS202I | G/T@734 | (9) |
| | rtM204V/I | A/G@739 | (4) |
| | | G/C/T@741 | |
| | rtM204S | T/G@740 | (15) |
| | | G/T@741 | |
| | rtV207I | G/A@748 | (16) |
| | | G/A/T/C@750 | |
| | rtS213T | T/A@766 | (11, 17) |
| | rtV214A | T/C@770 | (5) |
| Reverse transcriptase | rtQ215S | C/T@772 | (18) |
| | rtS219T | T/A@784 | (6) |
| | rtF221Y | T/A@791 | (19) |
| | rtS223A | T/G@796 | (20, 21) |
| | rtI224V | A/G@799 | (22) |
| | rtL229V/M | T/G/A@814 | (4, 23) |
| | rtI233V | A/G@826 | (24) |
| | rtH234Q | T/A/G@831 | (7) |
| | rtL235I | T/C/A@832 | (2) |
| | rtN236T | A/C@836 | (25) |
| | rtP237H | C/A@839 | (5) |
| | rtN/S/H/A238S | A/C/G@841 | (2, 5), |
| | | T/C@843 | |

TABLE 1-continued

Summary of mutations

| HBV Region | Amino acid substitutions | Nucleotide changes | Reference |
|---|---|---|---|
| | rtY245S | A/C@863 | (17) |
| | rtN/H248H | A/C@871 | (1, 2) |
| | rtM250V | A/G@877 | (9) |
| | rtV/I253I | G/A@886 | (1, 2) |
| Precore/Core | | G1896A | (26) |
| | | C1858T | (27) |
| Basal core promoter | | A1762T | (27) |
| | | G1764A | (27) |

The DNA molecules of an HV disclosed herein include, for example but not limited to, the coding sequences, the non-coding sequences of an HV, and fragments thereof. In some embodiments, the DNA molecule is a HBV reverse transcriptase gene, a HBV basal core/precore promoter, or a fragment thereof.

One or more different DNA molecules can be provided, where each DNA molecule includes at least one HV variation site of interest. In a particular embodiment, the HV variation sites are the HBV variation sites as listed in Table 1.

The DNA molecule can be provided from a sample of a subject suffering from an HV infection. The subject can either be the one who is treatment naive, or the one who is drug resistance. Exemplary samples include, but not limited to, hepatocytes, specimen of liver tissue, serum, plasma and blood of the subject. In some embodiments, the DNA molecule can be provided from samples of more than one subject.

In one embodiment the DNA molecule can be extracted and/or amplified from the sample as disclosed herein.

Extraction of the DNA molecule can be performed using a commercially available DNA preparation kit, in particular, a DNA extraction kit for an animal according to the manufacturer's protocol.

In some embodiments, the HV RNA is extracted from the sample of the subject and then reversed to the DNA molecule as disclosed herein. RNA extraction and reverse reaction can be performed using commercially available kits.

In some embodiments, before extending multiplex extension primers, amplification of the DNA molecule from the extracted DNA or RNA can be performed by means of PCR, RT-PCR, or the like using amplification primers. PCR, RT-PCR or the like can be performed using a commercially available kit according to the manufacturer's protocol. The thermal profile of PCR, RT-PCR or the like, or the optimization thereof can be determined or performed by an artisan given a specific DNA molecule to be amplified and specific amplification primers.

The amplification primers can be designed according to the DNA molecule to be amplified. In a preferred embodiment, the amplification primers can be designed by aligning genomic sequences from different HV genotypes. In another preferred embodiment, sequence tag(s) can be added to 5'-end of the amplification primers to increase their molecular weights for avoidance of any interference in mass spectra. In yet another preferred embodiment, the 5'- and 3'-portions of the DNA molecule correspond to the highly conserved genomic regions of an HV, where each portion represents an amplification primer.

The amplification primers can be 10-50 nucleotides in length, preferably 15-35 in length.

In some embodiments, the amplification can be a multiplex amplification when the HV variation sites are present in more than one DNA molecule. The multiplex can range from 2-plex to 50-plex, in particular, from 2-plex to 30-plex. The amplification primers can be multiplex amplification primers which are designed for different DNA molecules. In a preferred embodiment, the multiplex amplification primers are designed to avoid primer cross-hybridization. In a particular embodiment, the multiplex amplification primers are the primers having a 70%, 80%, 85%, preferably 90%, more preferably 95%, even more preferably 100% identity with those as set forth in SEQ ID NOs: 1-4.

In a particular embodiment, the DNA molecule is amplified by a 2-plex PCR using the primers as set forth in SEQ ID NOs: 1-4. The PCR reactions (25 µL) may contain 5 µL HBV DNA, 200 nM each of the primers (SEQ ID NOs: 1-2), 100 nM each of the primers (SEQ ID NOs: 3-4), 1× buffer (with 1.5 mM Mg2+), 1.0 mM additional Mg2+, 200 µM dNTP (each), and 0.5 units of Hotstar Taq polymerase (Qiagen). PCR may be initiated at 95° C. for 15 min, followed by 45 cycles of denaturation at 95° C. for 40 sec, annealing at 57° C. for 30 sec, and extension at 72° C. for 1.5 mM and a final extension at 72° C. for 3 min.

The DNA molecule may be provided after further treatment. The treatment can be dephosphorylation. In some embodiments, the amplified DNA molecule can be treated with a dephosphorylating reagent including, but not limited to, shrimp alkaline phosphatase (SAP).

In some embodiments, the multiplex extension as disclosed herein can preferably be a single nucleotide extension. The multiplex extension is used to extend the multiple primers to include nucleotides at more than one variation site of an HV. The extension can be in a direction of from 5' to 3' of an extension primer. The multiplex can range from 2-plex to 72-plex, in particular, from 2-plex to 36-plex. The extension can be performed using a commercially available primer extension kit. In particular, the primer extension kit is the one contained in MassARRAY iPLEX™ (Sequenom, Inc, San Diego, Calif.) for primer extension, an iPLEX™ reaction. The thermal profile of the extension or the optimization thereof can be determined or performed by an artisan.

In some embodiments, a standard thermal profile for MassARRAY iPLEX™ is employed as listed in FIG. 3. The extension reaction mixture may contain 7 µL of PCR-SAP products, 0.2 µL of 10× iPLEX buffer plus, 0.2 µL iPLEX termination mix with modified ddNTPs, 0.94 µL extension primer mixture, 0.041 µL iPLEX thermosequenase.

The multiplex extension primers are designed for more than one HV variation. Each multiplex extension primer can be designed based on its target HV variation site. In particular, a multiplex extension primer can be designed to be hybridizable to the immediate 3' downstream to a nucleotide at an HV variation site. More particularly, a multiplex extension primer can be complementary to the immediate 3' downstream to a nucleotide at an HV variation site. Even more particularly, the 3'-end of a multiplex extension primer can be complementary to the very nucleotide linked to the 3' of a nucleotide at an HV variation site.

In some embodiments, a multiplex extension primer can be a mixture of degenerate primers directed to the same target variation site where another one or more HV variation sites appear adjacent to the 3'-end of the nucleotide at the target variation site. In a preferred embodiment, a sequence tag can be added to 5'-end of a multiplex extension primer to increase its molecular weight for avoidance of any interference in mass spectra. The multiplex extension primers can be 10-50 nucleotides in length, particularly 15-35 in length, more particularly 15-28 in length.

The concentrations of multiplex extension primers can be adjusted to compensate differences in signal intensities in MS due to differences in sequence and molecular weight among different multiplex extension primers. Adjustments can be made based on real mass spectral data generated.

In one embodiment, the extension is 12-plex using the multiplex extension primers having a 70%, 80%, 85%, 90%, 95%, 96%, 97%, preferably 98%, more preferably 99%, even more preferably 100% identity with those as set forth in SEQ ID NOs: 5-16.

In another embodiment, the extension is 17-plex using the multiplex extension primers having a 70%, 80%, 85%, 90%, 95%, 96%, 97%, preferably 98%, more preferably 99%, even more preferably 100% identity with those as set forth in SEQ ID NOs: 17-33.

In yet another embodiment, the extension is 17-plex using the multiplex extension primers having a 70%, 80%, 85%, 90%, 95%, 96%, 97%, preferably 98%, more preferably 99%, even more preferably 100% identity with those as set forth in SEQ ID NOs: 34-50.

In still yet another embodiment, the extension is 14-plex using the multiplex extension primers having a 70%, 80%, 85%, 90%, 95%, 96%, 97%, preferably 98%, more preferably 99%, even more preferably 100% identity with those as set forth in SEQ ID NOs: 51-64.

The extension products disclosed herein, i.e. the extended multiplex extension primers, can be analyzed by MS, identifying the nucleotides at HV variation sites which are also contained in the extension products. MS analysis can be performed by a commercially available MS device according to the manufacturer's protocol. Data analysis can be performed using commercially available MS data analysis software.

In some embodiments, the MS can be matrix-assisted laser desorption/ionization-time-of-flight mass spectrometry (MALDI-TOF MS).

The MS analysis may comprise a step of extension product conditioning such as desaltification prior to sample loading on a MS device.

Another aspect is directed to a method for the treatment of a hepatitis virus (HV) infection in a subject, comprising the steps of a) detecting HV variations in the subject according to the detection method disclosed herein, wherein the HV variations are in association with drug resistance; b) assessing the drug resistance of the subject based on the detection; and c) treating the subject based on the assessment.

Yet another aspect is directed to a kit for the detection of hepatitis virus (HV) variations by mass spectrometry analysis, comprising multiplex extension primers disclosed herein.

In one embodiment, the multiplex extension primers are the primers having a 70%, 80%, 85%, 90%, 95%, 96%, 97%, preferably 98%, more preferably 99%, even more preferably 100% identity with those as set forth in SEQ ID NOs: 5-16.

In another embodiment, the multiplex extension primers are the primers having a 70%, 80%, 85%, 90%, 95%, 96%, 97%, preferably 98%, more preferably 99%, even more preferably 100% identity with those as set forth in SEQ ID NOs: 17-33.

In yet another embodiment, the multiplex extension primers are the primers having a 70%, 80%, 85%, 90%, 95%, 96%, 97%, preferably 98%, more preferably 99%, even more preferably 100% identity with those as set forth in SEQ ID NOs: 34-50.

In still yet another embodiment, the multiplex extension primers are the primers having a 70%, 80%, 85%, 90%, 95%, 96%, 97%, preferably 98%, more preferably 99%, even more preferably 100% identity with those as set forth in SEQ ID NOs: 51-64.

The kit may further comprise amplification primers as disclosed herein.

In a particular embodiment, the amplification primers are the primers having a 70%, 80%, 85%, preferably 90%, more preferably 95%, even more preferably 100% identity with those as set forth in SEQ ID NOs: 1-4.

The kit may still further comprise reagents for primer extension.

The kit may still further comprise reagents for primer extension, reagents for dephosphorylation, and/or reagents for PCR. In a particular embodiment, the kit may still further comprise the reagents as contained in MassARRAY iPLEX™.

EXAMPLES

Example 1

HBV Variation Selection

A literature search was performed to include all known HBV mutations that are directly associated with drug resistance. Variations in the precore (G1896A and C1858T) and basal core promoter (A1762T and G1764A) were included. Variations frequently observed during antiviral treatment, but not conclusively implicated in drug resistance were also included with the hope that when a large number of samples are analyzed in the future, statistical significance for their association with antiviral treatment may be observed for some of them. Summary of mutations are listed in Table 1.

Example 2

Sample Collection

A total of 168 patients with HBV infection were recruited for this study after obtaining informed consent. Out of these 168 patients, 88 patients had not received any antiviral therapy (treatment naive) and 80 patients had experienced a virological breakthrough with HBV DNA increase by >1 log from nadir level and to >100,000 copies/ml. About 1.5 mL serum samples were collected for each patient.

HBV DNA was extracted from serum using the QIAamp DNA Blood Mini Kit (Qiagen) according to the "DNA Purification from Blood or Body Fluids (Spin Protocol)". 800 µL serum was used for DNA extraction into 50 µL elution volume. Viral load of each sample was determined using a fluorescence PCR kit (PG Biotech, Shenzhen, China) (12).

HBV DNA ranged from $10^{3.07}$ to $10^{8.80}$ copies/mL (median: $10^{7.38}$) and $10^{3.42}$ to $10^{8.21}$ (median: $10^{5.39}$) copies/mL for the 88 treatment naive patients and the 80 drug resistant patients, respectively. The viral load in treatment naive samples was significantly higher than drug resistant samples (p<0.05, t-test).

Moreover, based on capillary sequencing of the samples from 32 treatment naive patients, 23 (71.9%) were genotype B HBV and 9 (28.1%) were genotype C HBV. The HBV DNA from thirty-three drug resistant samples was also sequenced. Twenty three (69.7%) patients were infected by genotype B HBV and 10 (30.3%) by genotype C HBV.

Example 3

HBV Variation Detection

Four main steps were involved in the detection of HBV variations by MALDI-TOF MS. The target HBV variations are listed in Table 1. Sequences and molecular weights of extension primers and extension products are provided in FIG. 6. All primers were synthesized by Integrated DNA Technologies (Coralville, Iowa). All other reagents were purchased from Sequenom (California, USA) unless otherwise specified.

Step 1: 2-Plex PCR to Amplify the HBV Regions of Interest

The reverse transcriptase and the basal core promoter/precore regions were selected since these two regions contain the functionally important variations as well as the variations frequently observed in patients undergoing antiviral therapy. We designed a 2-plex PCR assay which amplified all the target variations.

PCR primers were designed by aligning genomic sequences from different HBV genotypes (FIG. 4). PCR primer pairs were 5'-gttggatgGACTCGTGGTGGACTTCT CTCA-3' (251F-tag) (SEQ ID NO: 1) and 5'-ggatgCCCA-CAATTCKTTGACATACTT TCC-3' (1004R-tag) (SEQ ID NO: 2), and 5'-acgttggatgACCTCTGCACGTYRCATGGA-3' (1593F-tag) (SEQ ID NO: 3) and 5'-ggatgGAGAG-TAACTCCACAGTAGCTCCAA-3' (1950R-tag) (SEQ ID NO: 4), respectively. The non-capital letters were sequence tags to increase the molecular weights of the PCR primers so that they would not interfere in mass spectra.

The reverse transcriptase and the basal core promoter/precore regions were amplified by a 2-plex PCR using the PCR primer pairs above, generating two amplification products at a length of 754 bp and of 358 bp.

The 25 µL PCR reactions contained 5 µL HBV DNA, 200 nM each of the primers (251F-tag and 1004R-tag), 100 nM each of the primers (1593F-tag and 1950R-tag), 1× buffer (with 1.5 mM $Mg^{2+}$), 1.0 mM additional $Mg^{2+}$, 200 µM dNTP (each), and 0.5 units of Hotstar Taq polymerase (Qiagen).

PCR was initiated at 95° C. for 15 min, followed by 45 cycles of denaturation at 95° C. for 40 sec, annealing at 57° C. for 30 see, and extension at 72° C. for 1.5 min and a final extension at 72° C. for 3 min.

Upon further PCR optimization, this 2-plex PCR assay consistently amplified HBV DNA when the input DNA copy number was more than 94 copies per PCR. This allowed us to analyze all serum samples when the viral load was over 1170 copies/mL serum.

Step 2: Shrimp Alkaline Phosphatase (SAP) Treatment

To remove the remaining dNTPs in the PCR reactions, a 2-µL SAP solution including 1.53 µL of $H_2O$, 0.17 µL of SAP 10× buffer, and 0.5 units of SAP enzyme, was mixed with 5 µL of the PCR products. The reaction was performed at 37° C. for 40 min followed by inactivating at 85° C. for 5 min.

Step 3: Multiplex Primer Extension Reactions

MassARRAY Assay design (Sequenom) can achieve a multiplex level as high as 36. However, we decided to design assays at significantly lower multiplex levels so that new variations could be added with ease in future updates. As a result, the 60 target HBV variations were analyzed in 4 separate primer extension reactions (12-plex in assay 1, 17-plex in assay 2, 17-plex in assay 3, and 14-plex in assay 4).

60 extension primers were required for the 60 variations (FIG. 6).

The 9-µL extension reactions contained 7 µL of amplification-dephosphorylation products, 0.2 µL of 10× iPLEX buffer plus, 0.2 µL iPLEX termination mix with modified ddNTPs, 0.94 µL extension primer mixture, 0.041 µL iPLEX thermosequenase. A standard thermal profile for iPLEX reactions is listed in FIG. 3. The concentrations of the extension primers were further adjusted to compensate differences in signal intensities in mass spectra due to differences in sequence and molecular weight among different extension primers. Adjustments were made based on real mass spectral data generated. The concentration of each primer is listed in FIG. 6.

Step 4: MS Analysis

Extension products were desalted for MS analysis by adding 16 μL ddH$_2$O and 6 mg SpectroCLEAN resin. After centrifugation at 360 g for 5 min, approximately 15 mL of reaction solution was dispensed onto a 384-sample format SpectroCHIP using a Nanodispenser. Data acquisitions from SpectroCHIP were performed by Bruker Compact MALDI-TOF MS (Bruker Daltonics, Billerica, Mass., USA) and data analysis was carried out using TyperAnalyzer Application, version 4.0 (Sequenom, Inc.).

A representative mass spectrum for multiplex assay 1 is shown in FIG. 1.

Results

Upon optimizations of PCR and primer extension reactions, 88 treatment naive and 80 drug resistant serum samples were analyzed with a sensitivity close to 1,000 copies of HBV per milliliter of serum.

In this study, call rate was defined in two contexts: call rate per sample which was the successful call percentage for each individual sample among all variations; and call rate per variation which was the successful call percentage for each variation among all samples. When not specified, call rate referred to the successful call percentage for all variations among all samples.

To evaluate the performance of the HBV variation detection, we first looked at the call rate for each variation (defined as the percentage of successful calls in the selected samples tested for each variation). Thirty two variations (53.3%) achieved call rate over 98%. Fifty three variations (88.3%) achieved call rate over 90%. Fifty six out of the 60 variations (93.3%) achieved call rate over 80%. The overall call rate for all variations in all samples was 95.3%.

Figure 2:
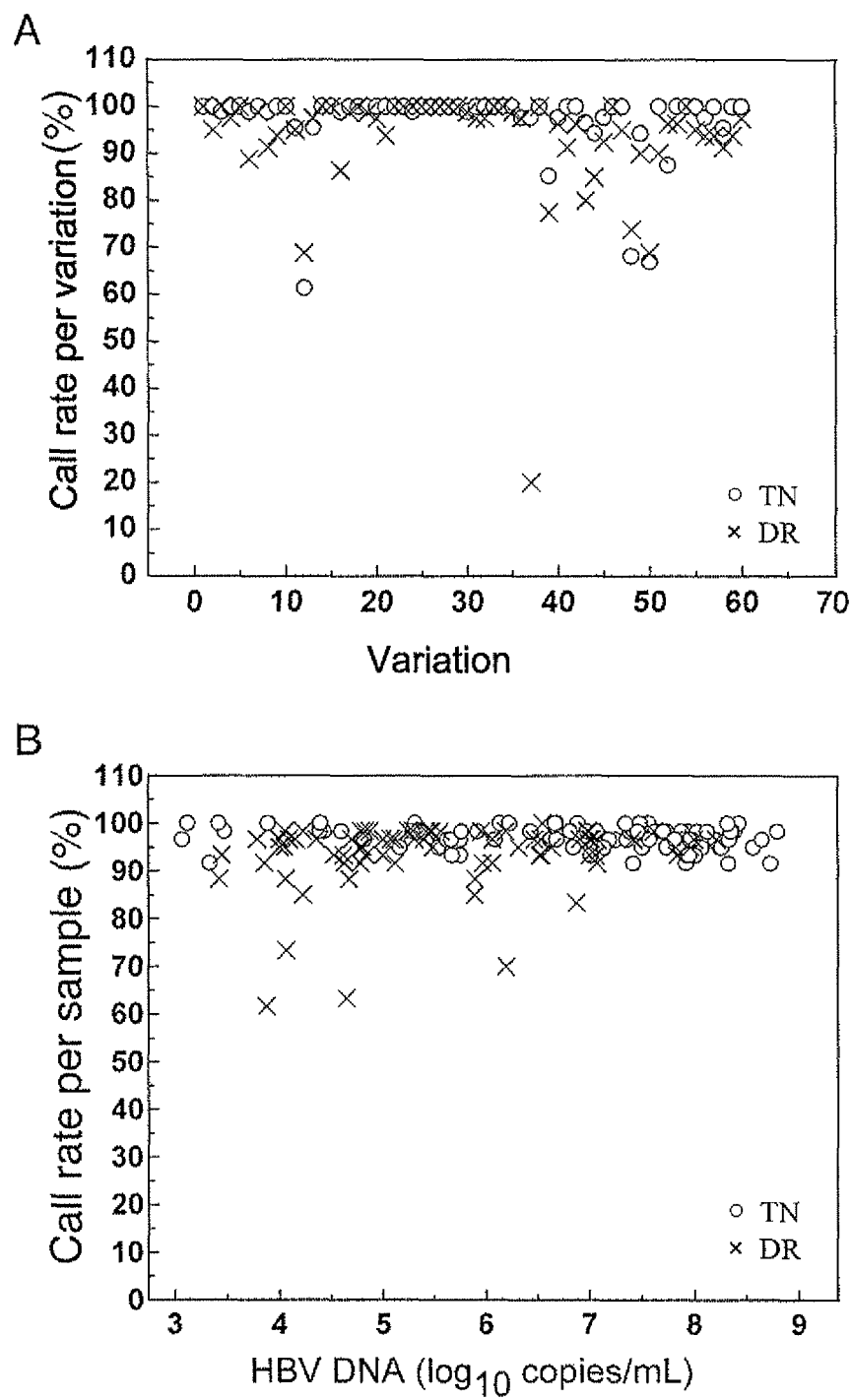
FIG. 2 is an illustration showing call rates for each variation and call rates for each sample. In panel a, call rates for each variation for each group (TN for treatment naive and DR for drug resistant) are shown. Majority of the variations had higher call rates (88.3% of the variations achieved a call rate over 90%). In panel b, call rates for each sample (shown by its viral load on the X axis) are shown. Drug resistant samples were more likely to have lower call rates. All samples with call rates <90% were drug resistant samples.

The call rates for each of the 60 variations in the two patient groups (treatment naive and drug resistant) are shown in FIG. 2a. The overall call rates for all variations in treatment naive and drug resistant samples were 97.0% and 93.4%, respectively. Additionally, call rates of 14 variations in drug resistant patients were significantly lower than that in treatment naive patients.

Call rates per sample (defined as the percentage of the successful calls for all 60 variations tested in each sample) were also analyzed. In FIG. 2b, call rates for each sample (its HBV viral load shown at X-axis) in the two patient groups were plotted. While call rates per sample remained high (>90%) over a wide range of concentrations for the treatment naive samples, a number of drug resistant samples had less than optimal call rates (7 with call rates 80-90% and 4 with call rates <80%).

Four of the 60 variations had call rates below 80%, which was the main reason for the overall no-call rate of 4.7%. None of these four variations has known functions. Additionally, there was a performance bias against drug resistant samples since all 11 samples with call rates below 90% were drug resistant samples.

Example 4

Capillary Sequencing Validation

A total of 70 samples (35 treatment naive and 35 drug resistant) were randomly selected for sequencing to validate MS results. The same PCR products used for SAP treatment (see Example 3) were used for direct sequencing using the BigDye Terminator Cycle Sequencing Kit, Version 3.0 (Applied Biosystems) and the ABI 3100 Genetic analyzer (Applied Biosystems).

The sequencing primers were

```
                                            (SEQ ID NO: 65)
5'-gttggatgGACTCGTGGTGGACTTCTCTCA-3' (PCR primer), (SEQ ID NO: 66)
5'-ggatgGAGAGTAACTCCACAGTAGCTCCAA-3' (PCR primer), (SEQ ID NO: 67)
5'-GYGCCATTTGTTCAGTGGTTCG-3'
and (SEQ ID NO: 68)
5'-AAACATAGAGGTTCCTTGAGCAGG-3'.
```

For the reverse transcriptase region, 27 treatment naive and 33 drug resistant samples were sequenced successfully. For the precore promoter and basal core promoter region, 29 treatment naive and 33 drug resistant samples were sequenced successfully. The overall sequencing success rate was 87%, although all the samples were successfully analyzed by MS.

Excluding some failed calls for certain variations in some samples, a total of 3,380 variation calls were obtained for both MS and direct sequencing. Overall, 3,340 variation calls (98.8%) were completely concordant between MS and sequencing, regardless of whether only a wild type or a mutant was present, or both sequences were present. For 23 variation calls (0.7%), MS detected both a wild type and a mutant while sequencing detected only a wild type or a mutant. One representative example is shown in FIG. 5a. For these calls, it is possible that sequencing missed the minor sequence (either wild type or mutant) due to a lower frequency of the minor variation (<20%). Some of these cases were validated by further cloning and sequencing.

For 12 variation calls (0.4%), sequencing detected both a wild type and a mutant while MS detected only wild type or mutant. Majority of these MS calls were of lower signal quality, which is likely to cause inability to detect a minor variation (FIG. 5b). For 0.1% of calls (5 out of 3,380 calls), direct sequencing and MS were completely discordant. Further cloning and sequencing confirmed that direct sequencing was correct. Highly consistent data were obtained between direct sequencing and MS, with only 5 variation calls out of 3,380 calls completely discordant. More frequently, MS detected the presence of both a wild type sequence and a mutation while direct sequencing did not. It should be noted that virtually all heterozygous calls from direct sequencing were done by careful manual inspection, while virtually all calls (homozygous or heterozygous) from MS were done automatically by the software. Additionally, sequencing reactions failed in 13% of the amplicons that were successfully analyzed by MS.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

REFERENCES

1. Seigneres B, Pichoud C, Ahmed S S, Hantz O, Trepo C, Zoulim F. Evolution of hepatitis B virus polymerase gene 1. sequence during famciclovir therapy for chronic hepatitis B. The Journal of infectious diseases 2000; 181:1221-33.
2. Stuyver L T, Locarnini S A, Lok A, Richman D D, Carman W F, Dienstag J L, Schinazi R F. Nomenclature for antiviral-resistant human hepatitis B virus mutations in the polymerase region. Hepatology (Baltimore, Md. 2001; 33:751-7.
3. Warner N, Locarnini S, Kuiper M, Bartholomeusz A, Ayres A, Yuen L, Shaw T. The L80I substitution in the reverse transcriptase domain of the hepatitis B virus polymerase is associated with lamivudine resistance and enhanced viral replication in vitro. Antimicrobial agents and chemotherapy 2007; 51:2285-92.
4. Allen M I, Deslauriers M, Andrews C W, Tipples G A, Walters K A, Tyrrell D L, et al. Identification and characterization of mutations in hepatitis B virus resistant to lamivudine. Lamivudine Clinical Investigation Group. Hepatology (Baltimore, Md. 1998; 27:1670-7.
5. Bartholomeusz A, Locarnini S. Hepatitis B virus mutations associated with antiviral therapy. Journal of medical virology 2006; 78 Suppl 1:S52-5.
6. Locarnini S. Hepatitis B viral resistance: mechanisms and diagnosis. Journal of hepatology 2003; 39 Suppl 1:S124-32.
7. Westland C E, Yang H, Delaney WEt, Gibbs C S, Miller M D, Wulfsohn M, et al. Week 48 resistance surveillance in two phase 3 clinical studies of adefovir dipivoxil for chronic hepatitis B. Hepatology (Baltimore, Md. 2003; 38:96-103.
8. Melegari M, Scaglioni P P, Wands J R. Hepatitis B virus mutants associated with 3TC and famciclovir administration are replication defective. Hepatology (Baltimore, Md. 1998; 27:628-33,
9. Tenney D J, Levine S M, Rose R E, Walsh A W, Weinheimer S P, Discotto L, et al. Clinical emergence of entecavir-resistant hepatitis B virus requires additional substitutions in virus already resistant to Lamivudine. Antimicrobial agents and chemotherapy 2004; 48:3498-507.
10. Delaney WEt, Yang H, Westland C E, Das K, Arnold E, Gibbs C S, et al. The hepatitis B virus polymerase mutation rtV173L is selected during lamivudine therapy and enhances viral replication in vitro. Journal of virology 2003; 77:11833-41.
11. Cane P A, Mutimer D, Ratcliffe D, Cook P, Beards G, Elias E, Pillay D. Analysis of hepatitis B virus quasispecies changes during emergence and reversion of lamivudine resistance in liver transplantation. Antiviral therapy 1999; 4:7-14.
12. Ono S K, Kato N, Shiratori Y, Kato J, Goto T, Schinazi R F, et al. The polymerase L528M mutation cooperates with nucleotide binding-site mutations, increasing hepatitis B virus replication and drug resistance. The Journal of clinical investigation 2001; 107:449-55.
13. Yatsuji H, Noguchi C, Hiraga N, Mori N, Tsuge M, Imamura M, et al. Emergence of a novel lamivudine-resistant hepatitis 13 virus variant with a substitution outside the YMDD motif. Antimicrobial agents and chemotherapy 2006; 50:3867-74.
14. Sheldon J, Camino N, Rodes B, Bartholomeusz A, Kuiper M, Tacke F, et al. Selection of hepatitis B virus polymerase mutations in HIV-coinfected patients treated with tenofovir. Antiviral therapy 2005; 10:727-34.
15. Bozdayi A M, Uzunalimoglu O, Turkyilmaz A R, Aslan N, Sezgin O, Sahin T, et al. YSDD: a novel mutation in HBV DNA polymerase confers clinical resistance to lamivudine. Journal of viral hepatitis 2003; 10:256-65.
16. Zollner B, Sterneck M, Wursthorn K, Petersen J, Schroter M, Laufs R, Feucht H H. Prevalence, incidence, and clinical relevance of the reverse transcriptase V207I mutation outside the YMDD motif of the hepatitis B virus polymerase during lamivudine therapy. Journal of clinical microbiology 2005; 43:2503-5.
17. Pallier C, Castera L, Soulier A, Hezode C, Nordmann P, Dhumeaux D, Pawlotsky J M. Dynamics of hepatitis 13 virus resistance to lamivudine. Journal of virology 2006; 80:643-53.
18. Bartholomeusz A, Locarnini S A. Antiviral drug resistance: clinical consequences and molecular aspects. Seminars in liver disease 2006; 26:162-70.
19. T. Pollicino, S. Maimone, G. Isgro, S. Brancatelli, G. Raffa, G. Caccamoa, et al. Variability of the HBV poi gene reverse-transcriptase domain in viral isolates from untreated and lamivudine-resistant chronic hepatitis B patients [Abstract]. Digestive and Liver Disease 2007; 39(3): A7.
20. Ahn S H, Chang H Y, Shim H J, Kim D Y, Paik Y H, Lee S K, et al. Evolution of viral quasisppecies in the polymerase gene of hepatitis B virus during antiviral treatment: from naive to viral breakthrough [Abstract]. Hepatology 2007; 46(81): 642A.
21. Tan J, Degertekin B, Wong S N, Husain M, Oberhelman K, Lok A S. Tenofovir monotherapy is effective in hepatitis B patients with antiviral treatment failure to adefovir in the absence of adefovir-resistant mutations. Journal of hepatology 2008; 48:391-8.
22. Yang H, Westland C E, Delaney WEt, Heathcote E J, Ho V, Fry J, et al. Resistance surveillance in chronic hepatitis B patients treated with adefovir dipivoxil for up to 60 weeks. Hepatology (Baltimore, Md. 2002; 36:464-73.
23. Liu C J, Chen P J, Lai M Y, Kao J H, Chen D S. Hepatitis B virus variants in patients receiving lamivudine treatment with breakthrough hepatitis evaluated by serial viral loads and full-length viral sequences. Hepatology (Baltimore, Md. 2001; 34:583-9.
24. Schildgen O, Simma H, Funk A, Olotu C, Wend U C, Hartmann H, et al. Variant of hepatitis B virus with primary resistance to adefovir. The New England journal of medicine 2006; 354:1807-12.
25. Angus P, Vaughan R, Xiang S, Yang H, Delaney W, Gibbs C, et al. Resistance to adefovir dipivoxil therapy associated with the selection of a novel mutation in the HBV polymerase. Gastroenterology 2003; 125:292-7.
26. Chen R Y, Edwards R, Shaw T, Colledge D, Delaney WEt, Isom H, et al. Effect of the G1896A precore mutation on drug sensitivity and replication yield of lamivudine-resistant HBV in vitro. Hepatology (Baltimore, Md. 2003; 37:27-35.
27. Tacke F, Gehrke C, Luedde T, Heim A, Manns M P, Trautwein C. Basal core promoter and precore mutations in the hepatitis B virus genome enhance replication efficacy of Lamivudine-resistant mutants. Journal of virology 2004; 78:8524-35.
28. Chen C J, Yang H I, Su J, Jen C L, You S L, Lu S N, et al. Risk of hepatocellular carcinoma across a biological gradient of serum hepatitis B virus DNA level. Jama 2006; 295:65-73.
29. Iloeje U H, Yang H I, Su J, Jen C L, You S L, Chen C J. Predicting cirrhosis risk based on the level of circulating hepatitis B viral load. Gastroenterology 2006; 130:678-86.
30. Chen G, Lin W, Shen F, Iloeje U H, London W T, Evans A A. Past HBV viral load as predictor of mortality and morbidity from HCC and chronic liver disease in a prospective study. Am J Gastroenterol 2006; 101:1797-803.

31. Chan H L, Tse C H, Mo F, Koh J, Wong V W, Wong G L, et al. High viral load and hepatitis B virus subgenotype ce are associated with increased risk of hepatocellular carcinoma. J Clin Oncol 2008; 26:177-82.

32. Lok A S, Lai C L, Leung N, Yao G B, Cui Z Y, Schiff E R, et al. Long-term safety of lamivudine treatment in patients with chronic hepatitis B. Gastroenterology 2003; 125:1714-22.

What is claimed is:

1. A method for the detection of hepatitis B virus (HBV) variations, comprising, a) providing an HBV DNA molecule from a subject suffering from an HBV infection as a template, wherein the DNA molecule includes an HBV variation site; b) extending multiplex extension primers along the template to obtain extension products containing nucleotides at the variation sites; and c) analyzing the extension products by mass spectrometry (MS) to detect the HBV variations, wherein the DNA molecule is provided by conducting a 2-plex PCR, wherein each primer has at least 70% identity to one of the primers set forth in SEQ ID NOs: 1-4, and wherein the multiplex extension primers are extended by using a set of primers selected from the group consisting of (i) the primers having at least 70% identity to those as set forth in SEQ ID NOs: 5-16 in a 12-plex reaction, (ii) the primers having at least a 70% identity with those as set forth in SEQ ID NOs: 17-33 in a 17-plex reaction, (iii) the primers having at least a 70% identity with those as set forth in SEQ ID NOs: 34-50 as set forth in a 17-plex reaction, and (iv) the primers having at least a 70% identity with those as set forth in SEQ ID NOs: 51-64 in a 14-plex reaction.

2. The method according to claim 1, wherein the template is provided after shrimp alkaline phosphatase (SAP) treatment.

3. The method according to claim 1, wherein the MS is matrix-assisted laser desorption/ionization-time-of-flight mass spectrometry (MALDI-TOF MS).

4. A method for the treatment of a hepatitis B virus (HBV) infection in a subject, comprising, a) detecting HBV variations in the subject according to the method of claim 1, wherein the HBV variations are in association with drug resistance; b) assessing the drug resistance of the subject based on the detection; and c) treating the subject based on the assessment.

5. The method according to claim 4, wherein the template is provided after shrimp alkaline phosphatase (SAP) treatment.

6. The method according to claim 4, wherein the MS is matrix-assisted laser desorption/ionization-time-of-flight mass spectrometry (MALDI-TOF MS).

7. A kit for the detection of hepatitis B virus (HBV) variations by mass spectrometry analysis, comprising multiplex extension primers as described in claim 1.

8. A kit for the detection of hepatitis B virus (HBV) variations by mass spectrometry analysis, comprising amplification primers as described in claim 1.

9. The kit according to claim 7, further comprising reagents for PCR.

10. The kit according to claim 7, further comprising reagents for primer extension.

11. The kit according to claim 7, further comprising reagents for dephosphorylation, preferably shrimp alkaline phosphatase (SAP).

* * * * *